(12) United States Patent
Chakravarty et al.

(10) Patent No.: US 7,972,692 B2
(45) Date of Patent: *Jul. 5, 2011

(54) BIODEGRADABLE MULTICOMPONENT FIBERS

(75) Inventors: Jayant Chakravarty, Woodbury, MN (US); Vasily Topolkaraev, Appleton, WI (US); Gregory J. Wideman, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 439 days.

This patent is subject to a terminal disclaimer.

(21) Appl. No.: 12/091,569

(22) PCT Filed: Dec. 15, 2005

(86) PCT No.: PCT/US2005/046178
§ 371 (c)(1),
(2), (4) Date: Apr. 25, 2008

(87) PCT Pub. No.: WO2007/070064
PCT Pub. Date: Jun. 21, 2007

(65) Prior Publication Data
US 2008/0227355 A1 Sep. 18, 2008

(51) Int. Cl.
*D02G 3/00* (2006.01)
*D04H 1/00* (2006.01)
*D04H 13/00* (2006.01)
(52) U.S. Cl. ......... 428/373; 442/361; 442/362; 442/364
(58) Field of Classification Search .................. 442/361, 442/362, 364; 428/373
See application file for complete search history.

(56) References Cited

U.S. PATENT DOCUMENTS

| | | |
|---|---|---|
| 5,039,783 A | 8/1991 | Brunelle et al. |
| 5,053,482 A | 10/1991 | Tietz |
| 5,108,820 A | 4/1992 | Kaneko et al. |
| 5,108,827 A | 4/1992 | Gessner |
| 5,188,885 A | 2/1993 | Timmons et al. |
| 5,231,161 A | 7/1993 | Brunelle et al. |
| 5,262,460 A | 11/1993 | Suzuki et al. |
| 5,270,401 A | 12/1993 | Sham et al. |
| 5,292,783 A | 3/1994 | Buchanan et al. |
| 5,336,552 A | 8/1994 | Strack et al. |
| 5,350,624 A | 9/1994 | Georger et al. |
| 5,382,400 A | 1/1995 | Pike et al. |
| 5,407,984 A | 4/1995 | Brunelle et al. |
| 5,432,000 A | 7/1995 | Young, Sr. et al. |
| 5,446,079 A | 8/1995 | Buchanan et al. |
| 5,464,688 A | 11/1995 | Timmons et al. |
| 5,466,517 A | 11/1995 | Eschwey et al. |

(Continued)

FOREIGN PATENT DOCUMENTS

EP 0731198 A2 9/1996

(Continued)

OTHER PUBLICATIONS

Showa Highpolymer Product Data, Bionelle.*

(Continued)

*Primary Examiner* — Norca L Torres-Velazquez
(74) *Attorney, Agent, or Firm* — Dority & Manning, P.A.

(57) ABSTRACT

A multicomponent fiber that contains a high-melting aliphatic polyester and a low-melting aliphatic polyester is provided. The multicomponent fibers are substantially biodegradable, yet readily processed into nonwoven structures that exhibit effective fibrous mechanical properties.

36 Claims, 4 Drawing Sheets

U.S. PATENT DOCUMENTS

| | | |
|---|---|---|
| 5,527,976 A | 6/1996 | Takekoshi et al. |
| 5,554,657 A | 9/1996 | Brownscombe et al. |
| 5,559,171 A | 9/1996 | Buchanan et al. |
| 5,580,911 A | 12/1996 | Buchanan et al. |
| 5,593,778 A | 1/1997 | Kondo et al. |
| 5,599,858 A | 2/1997 | Buchanan et al. |
| 5,614,298 A | 3/1997 | Tanaka et al. |
| 5,668,186 A | 9/1997 | Brunelle et al. |
| 5,688,582 A | 11/1997 | Nagaoka et al. |
| 5,753,736 A | 5/1998 | Bhat et al. |
| 5,783,505 A | 7/1998 | Duckett et al. |
| 5,817,199 A | 10/1998 | Brennecke et al. |
| 5,817,721 A | 10/1998 | Warzelhan et al. |
| 5,851,937 A | 12/1998 | Wu et al. |
| 5,895,710 A | 4/1999 | Sasse et al. |
| 5,900,322 A | 5/1999 | Buchanan et al. |
| 5,910,545 A | 6/1999 | Tsai et al. |
| 5,945,480 A | 8/1999 | Wang et al. |
| 5,952,433 A | 9/1999 | Wang et al. |
| 6,045,908 A | 4/2000 | Nakajima et al. |
| 6,063,895 A | 5/2000 | Chung et al. |
| 6,075,118 A | 6/2000 | Wang et al. |
| 6,090,494 A | 7/2000 | Rao |
| 6,177,193 B1 | 1/2001 | Tsai et al. |
| 6,194,483 B1 | 2/2001 | Tsai et al. |
| 6,197,860 B1 | 3/2001 | Tsai et al. |
| 6,201,068 B1 | 3/2001 | Tsai et al. |
| 6,218,321 B1 | 4/2001 | Lorcks et al. |
| 6,225,388 B1 | 5/2001 | Tsai et al. |
| 6,235,393 B1 | 5/2001 | Kimura et al. |
| 6,245,831 B1 | 6/2001 | Tsai et al. |
| 6,258,924 B1 | 7/2001 | Warzelhan et al. |
| 6,268,434 B1 | 7/2001 | Tsai et al. |
| 6,399,716 B2 | 6/2002 | Chung et al. |
| 6,420,027 B2 | 7/2002 | Kimura et al. |
| 6,420,048 B1 | 7/2002 | Wang |
| 6,495,656 B1 | 12/2002 | Haile et al. |
| 6,500,897 B2 | 12/2002 | Wang et al. |
| 6,506,873 B1 | 1/2003 | Ryan et al. |
| 6,525,164 B2 | 2/2003 | Faler |
| 6,544,455 B1 | 4/2003 | Tsai |
| 6,552,124 B2 | 4/2003 | Wang et al. |
| 6,552,162 B1 | 4/2003 | Wang et al. |
| 6,562,938 B2 | 5/2003 | Haile et al. |
| 6,576,576 B1 | 6/2003 | Wang et al. |
| 6,579,934 B1 | 6/2003 | Wang et al. |
| 6,607,996 B1 | 8/2003 | Matsunaga et al. |
| 6,623,853 B2 | 9/2003 | Branum et al. |
| 6,623,854 B2 | 9/2003 | Bond |
| 6,635,799 B1 | 10/2003 | Osborn, III et al. |
| 6,660,211 B2 | 12/2003 | Topolkaraev et al. |
| 6,686,303 B1 | 2/2004 | Haynes et al. |
| 6,709,526 B1 | 3/2004 | Bailey et al. |
| 6,713,595 B2 | 3/2004 | Chung et al. |
| 6,740,401 B1 | 5/2004 | Yahata et al. |
| 6,743,506 B2 | 6/2004 | Bond et al. |
| 6,756,412 B2 | 6/2004 | Muzzy |
| 6,783,854 B2 | 8/2004 | Bond |
| 6,787,493 B1 | 9/2004 | Nagaoka et al. |
| 6,802,895 B2 | 10/2004 | Mackey et al. |
| 6,811,740 B2 | 11/2004 | James et al. |
| 6,838,403 B2 | 1/2005 | Tsai et al. |
| 6,863,971 B2 | 3/2005 | Halahmi et al. |
| 6,872,674 B2 | 3/2005 | Williams et al. |
| 6,890,872 B2 | 5/2005 | Bond et al. |
| 6,890,989 B2 | 5/2005 | Wang et al. |
| 6,905,759 B2 | 6/2005 | Topolkaraev et al. |
| 6,946,195 B2 | 9/2005 | Griffith et al. |
| 6,946,506 B2 | 9/2005 | Bond et al. |
| 6,953,622 B2 | 10/2005 | Tsai et al. |
| 7,001,562 B2 | 2/2006 | Schiffer et al. |
| 7,029,620 B2 | 4/2006 | Gordon et al. |
| 7,037,983 B2 | 5/2006 | Huang et al. |
| 7,053,151 B2 | 5/2006 | Wang et al. |
| 7,060,867 B2 | 6/2006 | Jameson |
| 7,077,994 B2 | 7/2006 | Bond et al. |
| 7,101,623 B2 | 9/2006 | Jordan et al. |
| 7,153,569 B2 | 12/2006 | Kaufman et al. |
| 7,193,032 B2 | 3/2007 | Culbert et al. |
| 7,241,838 B2 | 7/2007 | Shelby et al. |
| 7,368,503 B2 | 5/2008 | Hale |
| 7,468,335 B2 | 12/2008 | Imes et al. |
| 2002/0127939 A1 | 9/2002 | Hwo et al. |
| 2002/0168912 A1 | 11/2002 | Bond et al. |
| 2003/0022569 A1 | 1/2003 | Lee et al. |
| 2003/0022581 A1 | 1/2003 | Tsai et al. |
| 2003/0092343 A1 | 5/2003 | Bond et al. |
| 2003/0134915 A1 | 7/2003 | Scantlebury et al. |
| 2003/0176136 A1 | 9/2003 | Wadsworth |
| 2003/0191442 A1 | 10/2003 | Bewick-Sonntag et al. |
| 2004/0000313 A1 | 1/2004 | Gaynor et al. |
| 2004/0002273 A1 | 1/2004 | Fitting et al. |
| 2004/0053047 A1 | 3/2004 | Jackson et al. |
| 2004/0102123 A1 | 5/2004 | Bowen, Jr. et al. |
| 2004/0126578 A1* | 7/2004 | Tsai et al. ................ 428/373 |
| 2004/0132873 A1 | 7/2004 | Bailey et al. |
| 2005/0054999 A1 | 3/2005 | Morman et al. |
| 2005/0112350 A1 | 5/2005 | Ning |
| 2005/0112363 A1 | 5/2005 | Ning |
| 2005/0208294 A1 | 9/2005 | Kaufman et al. |
| 2007/0082573 A1 | 4/2007 | Noda et al. |
| 2007/0219339 A1 | 9/2007 | Fregoso-Infante et al. |

FOREIGN PATENT DOCUMENTS

| | | |
|---|---|---|
| EP | 0731198 A3 | 9/1996 |
| EP | 0905292 A1 | 3/1999 |
| EP | 1397536 B1 | 3/2004 |
| EP | 1397537 B1 | 3/2004 |
| EP | 1397538 B1 | 3/2004 |
| EP | 1397539 B1 | 3/2004 |
| JP | 7109659 | 4/1995 |
| JP | 7125128 | 5/1995 |
| JP | 11043857 | 2/1999 |
| JP | 11050369 | 2/1999 |
| JP | 11117164 | 4/1999 |
| JP | 11286864 | 10/1999 |
| JP | 2001172829 A | 6/2001 |
| JP | 2003064568 | 3/2003 |
| JP | 2003193349 A | 7/2003 |
| JP | 2005048350 A | 2/2005 |
| WO | WO 9850611 A1 | 11/1998 |
| WO | WO 02090629 A1 | 11/2002 |
| WO | WO 02090630 A1 | 11/2002 |
| WO | WO 2004061172 A2 | 7/2004 |
| WO | WO 2004061172 A3 | 7/2004 |
| WO | WO 2007070064 A1 | 6/2007 |
| WO | WO 2008008067 A1 | 1/2008 |
| WO | WO 2008008068 A1 | 1/2008 |
| WO | WO 2008008074 A1 | 1/2008 |
| WO | WO 2008073099 A1 | 6/2008 |

OTHER PUBLICATIONS

Abstract of Korean Patent No. KR1020010057068A, Jul. 4, 2001.
Abstract of Korean Patent No. KR1020030022514A, Mar. 17, 2003.
Abstract of Korean Patent No. KR1020040005193A, Jan. 16, 2004.
Abstract of Korean Patent No. KR1020040005194A, Jan. 16, 2004.
ASTM D 1117-97—*Standard Test Methods for Nonwoven Fabrics*, Mar. 10, 1997, pp. 311-313.
ASTM D 1238-04c—*Standard Test Method for Melt Flow Rates of Thermoplastics by Extrusion Plastometer*, current edition approved Dec. 1, 2004, originally approved in 1965, pp. 1-14.
ASTM D 1239-92—*Standard Test Method for Resistance of Plastic Films to Extraction by Chemicals*, current edition approved Aug. 15, 1992, pp. 281-282.
ASTM D 3418-03 (D 3417-99)—*Standard Test Method for Transition Temperatures and Enthalpies of Fusion and Crystallization of Polymers by Differential Scanning Calorimetry*, current edition approved Dec. 1, 2003, originally approved in 1975, pp. 66-72.
ASTM D 5034-95—*Standard Test Method for Breaking Strength and Elongation of Textile Fabrics (Grab Test)*, current edition approved May 15, 1995, pp. 674-681.

ASTM D 5338-92—*Standard Test Method for Determining Aerobic Biodegradation of Plastic Materials Under Controlled Composting Conditions*, current edition approved Dec. 15, 1992, pp. 456-461.

ASTM D 7191-05—*Standard Test Method for Determination of Moisture in Plastics by Relative Humidity Sensor*, current edition approved Nov. 1, 2005, pp. 1-4.

Article—*Biodegradation of aliphatic-aromatic copolyesters: evaluation of the final biodegradability and ecotoxicological impact of degradation intermediates*, Witt et al., Chemosphere 44, 2001, pp. 289-299.

Article—*Rheological Properties of Poly(lactides). Effect of Molecular Weight and Temperature on the Viscoelasticity of Poly(l-lactic acid)*, Cooper-White et al., Journal of Polymer Science: Part B: Polymer Physics, vol. 37, 1999, pp. 1803-1814.

Article—*Synthesis of Oligoester α,ω-diols by Alcoholysis of PET through the Reactive Extrusion Process*, Dannoux et al., The Canadian Journal of Chemical Engineering, vol. 80, Dec. 2002, pp. 1075-1082.

Product Information on Ecoflex® from BASF—The Chemical Company, Sep. 22, 2005, 4 pages.

Product Information from Ingeo and NatureWorks®—PLA Polymer 6201D, 6202D, and 6302D, 2005, 11 pages.

Search Report and Written Opinion for PCT/US2005/046178, Sep. 1, 2006, 15 pages.

Related U.S. Patent Applications.

* cited by examiner

BIODEGRADABLE MULTICOMPONENT FIBERS

BACKGROUND OF THE INVENTION

Disposable absorbent articles generally contain absorbent fibrous webs, such as airlaid or bonded carded webs. Such webs are often stabilized with binder fibers during web formation. More specifically, the binder fibers are normally multicomponent fibers with a significant difference, i.e. at least 20° C., in melt temperature between the higher-melting and the lower-melting components. The fibers are thus heated at a temperature sufficient to melt the lower-melting components, but not the higher melting components. Several binder fibers have been developed that are biodegradable to enhance the disposability of the absorbent article. Many commercially-available biodegradable polymers are formed from aliphatic polyester materials. Although fibers prepared from aliphatic polyesters are known, problems have been encountered with their use. For example, aliphatic polyesters have a relatively slow crystallization rate in comparison to polyolefin polymers, thereby often resulting in poor processability. Most aliphatic polyesters also have much lower melting temperatures than polyolefins and are difficult to sufficiently cool following thermal processing. In addition, many aliphatic polyesters (e.g., poly(lactic acid)) undergo severe heat-shrinkage due to the relaxation of the polymer chain during downstream heat treatment processes, such as thermal bonding and lamination. Thus, biodegradable binder fibers were developed in response to these and other problems. One such binder fiber is described in U.S. Pat. No. 6,177,193 to Tsai, et al. The binder fiber of Tsai, et al. is formed from two components, one of which is a blend of an aliphatic polyester, multicarboxylic acid, and wetting agent. The multicarboxylic acid is required to reduce the viscosity of the polymer for processing, as well as to facilitate crystallization (i.e., nucleating agent) during quenching. One problem with such fibers, however, is that they require a manufacturing process that is relatively complex and inefficient. In addition, the fibers are also weak and have a relatively low tensile strength.

As such, a need currently exists for a fiber that is biodegradable and easily processed into fibrous structures that exhibit good mechanical properties.

SUMMARY OF THE INVENTION

In accordance with one embodiment of the present invention, a biodegradable multicomponent fiber is disclosed. The fiber comprises a first component that contains at least one high-melting point aliphatic polyester having a melting point of from about 160° C. to about 250° C. The fiber also comprises a second component that contains at least one low-melting point aliphatic polyester, the melting point of the low-melting point aliphatic polyester being at least about 30° C. less than the melting point of the high-melting point aliphatic polyester. The low-melting point aliphatic polyester has a number average molecular weight of from about 30,000 to about 120,000 Daltons and an apparent viscosity of from about 50 to about 215 Pascal-seconds, as determined at a temperature of 160° C. and a shear rate of 1000 $sec^{-1}$. The present inventors have discovered that polymers having this particular combination of molecular weight and viscosity may possess enhanced processability without adversely affecting the strength and bonding capacity of the resulting fiber.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 2 shows SEM microphotographs (40×) of two fiber samples formed in Example 3, wherein

Figure 1:
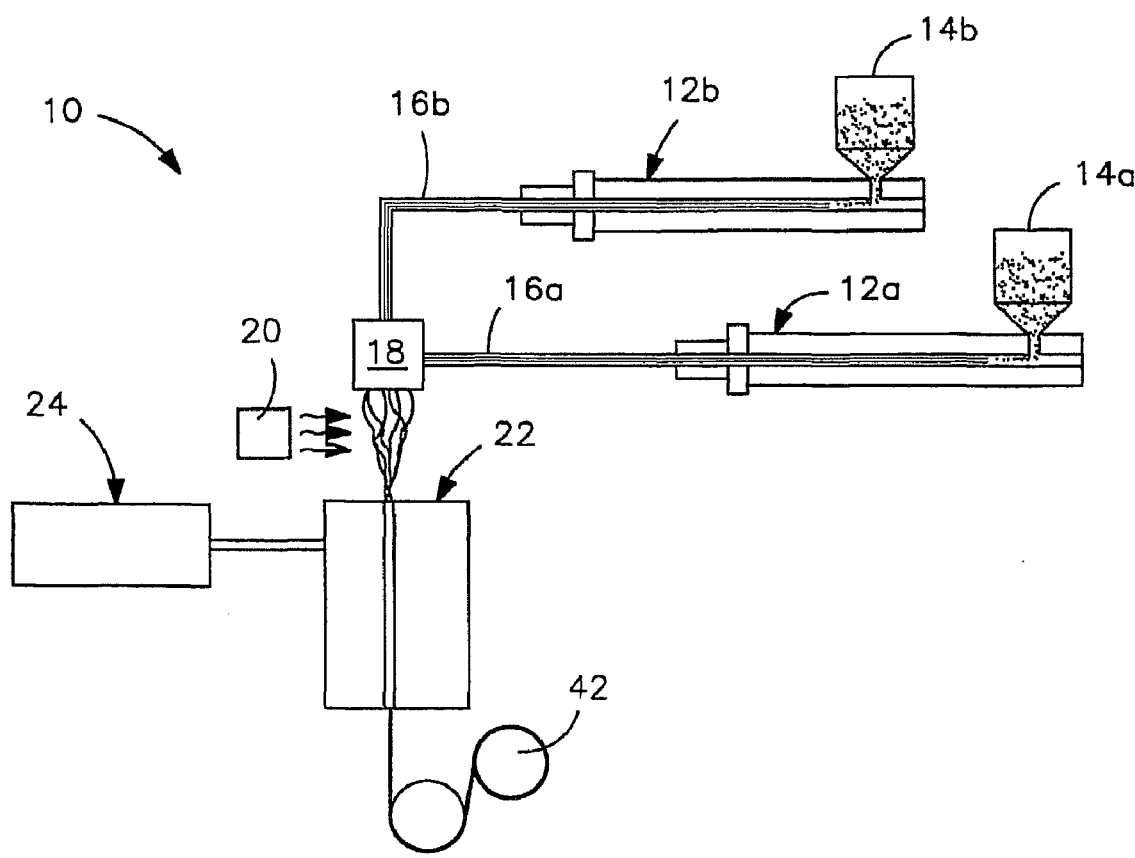
FIG. 1 is a schematic illustration of a process that may be used in one embodiment of the present invention to form multicomponent fibers.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

DEFINITIONS

As used herein, the term "biodegradable" or "biodegradable polymer" generally refers to a material that degrades from the action of naturally occurring microorganisms, such as bacteria, fungi, and algae; environmental heat; moisture; or other environmental factors. The biodegradability of a material may be determined using ASTM Test Method 5338.92.

As used herein, the term "fibers" refer to elongated extrudates formed by passing a polymer through a forming orifice such as a die. Unless noted otherwise, the term "fibers" includes discontinuous strands having a definite length and continuous strands of material, such as filaments.

As used herein, the term "multicomponent" refers to fibers formed from at least two polymer components (e.g., bicomponent fibers).

As used herein, the term "nonwoven web" refers to a web having a structure of individual fibers or threads that are interlaid, but not in an identifiable manner as in a knitted fabric. Nonwoven webs include, for example, meltblown webs, spunbond webs, carded webs, wet-laid webs, airlaid webs, coform webs, hydraulically entangled webs, etc.

As used herein, the term "bonded carded web" refers to a web made from staple fibers that are sent through a combing or carding unit, which separates or breaks apart and aligns the staple fibers in the machine direction to form a generally machine direction-oriented fibrous nonwoven web. Such fibers are usually obtained in bales and placed in an opener/blender or picker, which separates the fibers prior to the carding unit. Once formed, the web is then bonded by one or more known methods.

As used herein, the term "airlaid web" refers to a web made from bundles of fibers having typical lengths ranging from about 3 to about 19 millimeters (mm). The fibers are separated, entrained in an air supply, and then deposited onto a forming surface, usually with the assistance of a vacuum supply. Once formed, the web is then bonded by one or more known methods.

As used herein, the term "coform web" generally refers to a composite material containing a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

DETAILED DESCRIPTION

The present invention is directed to a biodegradable multicomponent fiber containing a first component formed from at least one high-melting aliphatic polyester and a second component formed from at least one low-melting aliphatic polyester component. The first and second components may be arranged in any desired configuration to form multicomponent fibers in accordance with the present invention. The configuration of such materials may be, for example, a sheath-core, side-by-side, pie, island-in-the-sea, and so forth. The resulting multicomponent fibers are substantially biodegradable, yet readily processed into fibrous structures that exhibit good mechanical properties.

I. First Component

As stated, the first component of the multicomponent fibers is formed from one or more "high melting point" biodegradable aliphatic polyesters. Typically, the melting point of such polyesters is from about 160° C. to about 250° C., in some embodiments from about 170° C. to about 240° C., and in some embodiments, from about 180° C. to about 220° C. Various "high melting point" aliphatic polyesters may be employed in the present invention, such as polyesteramides, modified polyethylene terephthalate, polylactic acid (PLA), terpolymers based on polylactic acid, polyglycolic acid, polyalkylene carbonates (such as polyethylene carbonate), polyhydroxyalkanoates (PHA), polyhydroxybutyrates (PHB), polyhydroxyvalerates (PHV), and polyhydroxybutyrate-hydroxyvalerate copolymers (PHBV). The term "polylactic acid" generally refers to homopolymers of lactic acid, such as poly(L-lactic acid), poly(D-lactic acid), poly(DL-lactic acid), mixtures thereof, and copolymers containing lactic acid as the predominant component and a small proportion of a copolymerizable comonomer, such as 3-hydroxybutyrate, caprolactone, glycolic acid, etc.

Any known polymerization method, such as polycondensation or ring-opening polymerization, may be used to polymerize lactic acid. In the polycondensation method, for example, L-lactic acid, D-lactic acid, or a mixture thereof is directly subjected to dehydro-polycondensation. In the ring-opening polymerization method, a lactide that is a cyclic dimer of lactic acid is subjected to polymerization with the aid of a polymerization-adjusting agent and catalyst. The lactide may include L-lactide (a dimer of L-lactic acid), D-lactide (a dimer of D-lactic acid), DL-lactide (a condensate of L-lactic acid and D-lactic acid), or mixtures thereof. These isomers may be mixed and polymerized, if necessary, to obtain polylactic acid having any desired composition and crystallinity. A small amount of a chain-extending agent (e.g., a diisocyanate compound, an epoxy compound or an acid anhydride) may also be employed to increase the molecular weight of the polylactic acid. Generally speaking, the weight average molecular weight of the polylactic acid is within the range of about 60,000 to about 1,000,000. One particularly suitable polylactic acid polymer that may be used in the present invention is commercially available from Biomer, Inc. (Germany) under the name Biomer™ L9000. Still other suitable polylactic acid polymers are commercially available from Natureworks, LLC of Minneapolis, Minn.

II. Second Component

The second component is formed from one or more "low melting point" biodegradable aliphatic polyesters. Typically, such polyesters have a melting point of from about 50° C. to about 160° C., in some embodiments from about 100° C. to about 160° C., and in some embodiments, from about 120° C. to about 160° C. Moreover, the melting point is also typically at least about 30° C., in some embodiments at least about 40° C., and in some embodiments, at least about 50° C. less than the melting point of the "high melting point" aliphatic polyesters. "Low melting point" aliphatic polyesters are useful in that they biodegrade at a faster rate than the high melting point polyesters. In addition, they are generally softer to the touch than most "high melting point" aliphatic polyesters. The glass transition temperature ("$T_g$") of the low melting point polyesters may also be less than that of the high melting point polyesters to improve flexibility and processability of the polymers. For example, the low melting point aliphatic polyesters may have a $T_g$ of about 25° C. or less, in some embodiments about 0° C. or less, and in some embodiments, about −10° C. or less. Such a glass transition temperature may be at least about 5° C., in some embodiments at least about 10° C., and in some embodiments, at least about 15° C. less than the glass transition temperature of the high melting point polyesters.

Examples of aliphatic polyesters that may have a low melting point and glass transition temperature include aliphatic polyesters with repeating units of at least 5 carbon atoms (e.g., polyhydroxyvalerate, polyhydroxybutyrate-hydroxyvalerate copolymer and polycaprolactone), and succinate-based aliphatic polymers (e.g., polybutylene succinate, polybutylene succinate adipate, and polyethylene succinate). More specific examples may include polyethylene oxalate, polyethylene malonate, polyethylene succinate, polypropylene oxalate, polypropylene malonate, polypropylene succinate, polybutylene oxalate, polybutylene malonate, polybutylene succinate, and blends and copolymers of these compounds. Among these compounds, polybutylene succinate and copolymers thereof are normally preferred.

Aliphatic polyesters are typically synthesized through the condensation polymerization of a polyol and an aliphatic dicarboxylic acid or an anhydride thereof. The polyols may be substituted or unsubstituted, linear or branched, polyols selected from polyols containing 2 to about 8 carbon atoms, polyalkylene ether glycols containing 2 to 8 carbon atoms, and cycloaliphatic diols containing about 4 to about 12 carbon atoms. Substituted polyols typically contain 1 to about 4 substituents independently selected from halo, $C_6$-$C_{10}$ aryl and $C_1$-$C_4$ alkoxy. Examples of polyols that may be used include, but are not limited to, ethylene glycol, diethylene glycol, propylene glycol, 1,3-propanediol, 2,2-dimethyl-1,3-propanediol, 1,3-butanediol, 1,4-butanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, and tetraethylene glycol. Preferred polyols include 1,4-butanediol; 1,3-propanediol; ethylene glycol; 1,6-hexanediol; diethylene glycol; and 1,4-cyclohexanedimethanol. Representative aliphatic dicarboxylic acids that may be used include substituted or unsubstituted, linear or branched, non-aromatic dicarboxylic acids selected from aliphatic dicarboxylic acids containing 2 to about 12 carbon atoms and cycloaliphatic dicarboxylic acids containing about 5 to about 10 carbon atoms. The substituted non-aromatic dicarboxylic acids will typically contain 1 to about 4 substituents selected from halo, $C_6$-$C_{10}$ aryl, and $C_1$-$C_4$ alkoxy. Non-limiting examples of aliphatic and cycloaliphatic dicarboxylic acids include malonic, succinic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. The polymerization is catalyzed by a catalyst, such as a titanium-based catalyst (e.g., tetraisopropyltitanate, tetraisopropoxy titanium, dibutoxydiacetoacetoxy titanium, or tetrabutyltitanate).

If desired, a diisocyanate chain extender may be reacted with the aliphatic polyester prepolymer to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri- or polyisocyanates. The preferred diisocyanate is hexamethylene diisocyanate. The amount of the chain extender employed is typically from about 0.3 to about 3.5 wt. %, in some embodiments, from about 0.5 to about 2.5 wt % based on the total weight percent of the polymer.

The aliphatic polyesters may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, glycerol, 1,2,4-butanetriol, pentaerythritol, 1,2,6-hexanetriol, sorbitol, 1,1,4,4,-tetrakis(hydroxymethyl)cyclohexane, tris(2-hydroxyethyl)isocyanurate, and dipentaerythritol. Representative higher molecular weight polyols (molecular weight of 400 to 3000) that may be used as branching agents include triols derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethanetetracarboxylic acid, 1,1,2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

Polycaprolactone polymers may also be used in the present invention. Polycaprolactone polymers are generally prepared by the polymerization of ε-caprolactone, which is a seven-member ring compound that is characterized by its reactivity. Cleavage usually takes place at the carbonyl group. Higher molecular weight polycaprolactone may be prepared under the influence of a wide variety of catalysts, such as aluminum alkyls, organometallic compositions, such as Group IA, IIA, IIB, or IIIA metal alkyls, Grignard reagents, Group II metal dialkyls, calcium or other metal amides or alkyl amides, reaction products of alkaline earth hexamoniates, alkaline oxides and acetonitrile, aluminum trialkoxides, alkaline earth aluminum or boron hydrides, alkaline metal or alkaline earth hydrides or alkaline metals alone. An initiator may also be used in the preparation of polycaprolactone, such as an aliphatic diol that forms a terminal end group. Examples of polycaprolactone polymers that may be suitable for use in the present invention include a variety of polycaprolactone polymers that are available from Union Carbide Corporation, Somerset, N.J., under the designation TONE™ Polymer P767E and TONE™ Polymer P787 polycaprolactone polymers.

The low melting point aliphatic polyesters described above are primarily aliphatic in nature, i.e., the monomer constituents are primarily aliphatic, to optimize biodegradability. For example, the low melting point aliphatic polyesters typically contain at least about 50 mol. %, in some embodiments at least about 60 mol. %, and in some embodiments, at least about 70 mol. % of aliphatic monomer(s). Although primarily aliphatic in nature, the low melting point polyesters may nevertheless contain a minor portion of other monomer constituents, such as aromatic monomers (e.g., terephtalic acid) that further improve the strength and tenacity of the fibers. When utilized, the aromatic monomers may, for example, constitute from about 1 mol. % to about 50 mol. %, in some embodiments from about 10 mol. % to about 40 mol. %, and in some embodiments, from about 15 mol. % to about 30 mol. % of the low melting point aliphatic polyester. One particular example of an aliphatic polyester containing an aromatic terephtalic acid monomer (~22 mol. %) constituent is available under the designation Ecoflex™ F BX 7011 from BASF Corp. Another example of an aliphatic polyester containing an aromatic terephtalic acid monomer (~25 mol. %) constituent is available under the designation Enpol™ 8060M from IRE Chemicals (South Korea).

Regardless of their particular type, the present inventors have discovered that "low melting point" aliphatic polyesters having a certain combination of thermal and mechanical properties may provide improved processability and strength to the resulting multicomponent fibers. For example, aliphatic polyesters having too great of a molecular weight generally possess heavily entangled polymer chains and thus result in a thermoplastic composition that is difficult to process. Conversely, aliphatic polyesters having too low of a molecular weight do not generally possess enough entanglement, which leads to a relatively weak melt strength. Thus, the "low melting point" aliphatic polyesters employed in the present invention typically have a number average molecular weight ("$M_n$") ranging from about 30,000 to about 120,000 Daltons, in some embodiments from about 40,000 to about 100,000 Daltons, and in some embodiments, from about 45,000 to about 85,000 Daltons. Likewise, the "low melting point" aliphatic polyesters also typically have a weight average molecular weight ("$M_w$") ranging from about 30,000 to about 240,000 Daltons, in some embodiments from about 50,000 to about 190,000 Daltons, and in some embodiments, from about 60,000 to about 105,000 Daltons. The molecular weight distribution of the selected polymers is also relatively narrow to enhance polymer processing and provide more consistent properties. That is, the ratio of the weight average molecular weight to the number average molecular weight ("$M_w/M_n$"), i.e., the "polydispersity index", is relatively low. For example, the polydispersity index typically ranges from about 1.0 to about 3.0, in some embodiments from about 1.2 to about 2.0, and in some embodiments, from about 1.4 to about 1.8. The weight and number average molecular weights may be determined by methods known to those skilled in the art.

To provide improved processability, the "low melting point" aliphatic polyester is also selected to have an apparent viscosity within a certain range. More specifically, aliphatic polyesters having too great of an apparent viscosity will generally be difficult to process. On the other hand, aliphatic polyesters having too low of an apparent viscosity will generally result in an extruded fiber lacking tensile strength and sufficient bonding capacity. Thus, in most embodiments, the "low melting point" aliphatic polyester has an apparent viscosity of from about 50 to about 215 Pascal seconds (Pa·s), in some embodiments from about 75 to about 200 Pa·s, and in some embodiments, from about 80 to about 150 Pa·s, as determined at a temperature of 160° C. and a shear rate of 1000 sec$^{-1}$. The present inventors have discovered that the particular combination of molecular weight and viscosity set forth above results in polymers having enhanced processability without adversely affecting the strength and bonding capacity of the resulting fiber.

The melt flow index of the "low melting point" aliphatic polyesters may also be selected within a certain range to optimize the properties of the resulting fibers. The melt flow index is the weight of a polymer (in grams) that may be forced through an extrusion rheometer orifice (0.0825-inch diameter) when subjected to a force of 2160 grams in 10 minutes at 190° C. Generally speaking, the melt flow index is high enough to improve melt processability, but not so high as to adversely interfere with the binding properties of the fibers. Thus, in most embodiments of the present invention, the "low melting point" aliphatic polyesters have a melt flow index of from about 5 to about 200 grams per 10 minutes, in some embodiments from about 15 to about 160 grams per 10 minutes, and in some embodiments, from about 20 to about 120 grams per 10 minutes, measured in accordance with ASTM Test Method D1238-E.

The crystallinity of the aliphatic polyester also influences the properties of the resulting multicomponent fibers. That is, polymers having a higher degree of melt and crystallization enthalpy are more readily incorporated into bonded web products. For example, such polymers are more readily able to bond at higher speeds and also have a lower degree of shrinkage, thereby improving web stability, tensile strength, and web aesthetics. Thus, the aliphatic polyesters are typically selected to have a degree of crystallinity or latent heat of fusion ($\Delta H_f$) of greater than about 25 Joules per gram ("J/g"), in some embodiments greater than about 35 J/g, and in some embodiments, greater than about 50 J/g. Likewise, the aliphatic polyesters are also typically selected to have a latent heat of crystallinity ($\Delta H_c$) of greater than about 35 Joules per gram ("J/g"), in some embodiments greater than about 50 J/g, and in some embodiments, greater than about 60 J/g.

One difficulty encountered in the thermal processing of aliphatic polyester polymers into fibers is the sticky nature of these polymers. Attempts to draw the fibers, either mechanically, or through an air drawing process, will often result in the aggregation of the fibers into a solid mass. Thus, in accordance with the present invention, the "low melting point" aliphatic polyesters are also selected to have a relatively high crystallization temperature ("$T_c$"), thereby reducing tackiness. Specifically, the crystallization temperature may range from about 40° C. to about 100° C., in some embodiments from about 50° C. to about 90° C., and in some embodiments, from about 60° C. to about 80° C. As discussed in more detail below, the latent heat of fusion ($\Delta H_f$), latent heat of crystallization ($\Delta H_c$), and crystallization temperature may all be determined using differential scanning calorimetry ("DSC") in accordance with ASTM D-3417.

Any of a variety of "low melting point" aliphatic polyester polymers may possess the desired thermal and mechanical properties referenced above. In particular embodiments of the present invention, for instance, polybutylene succinate copolyesters are employed as the second component of the multicomponent fibers. One specific example of a suitable polybutylene succinate polymers is commercially available from IRE Chemicals (South Korea) under the designation Enpol™ G4500.

A beneficial aspect of the present invention is that the above-described thermal and mechanical properties of the "low melting point" aliphatic polyesters may be provided without the need for conventional additives. For example, many conventional biodegradable thermoplastic compositions require the use of a nucleating agent to improve processing and to facilitate crystallization during quenching. One type of such a nucleating agent is a multi-carboxylic acid, such as succinic acid, glutaric acid, adipic acid, pimelic acid, suberic acid, azelaic acid, sebacic acid, and mixtures of such acids, as described in U.S. Pat. No. 6,177,193 to Tsai, et al. The present inventors have discovered, however, that through the careful selection of an aliphatic polyester having certain thermal and physical properties, such nucleating agents are not necessarily required. In fact, the present inventors have discovered that excellent results may be achieved using aliphatic polyesters as the principal ingredient of the second component. That is, the aliphatic polyesters may constitute at least about 90 wt. %, in some embodiments at least about 92 wt. %, and in some embodiments, at least about 95 wt. % of the second component. Nevertheless, it should be understood that nucleating agents may be used in some embodiments of the present invention. When utilized, however, the nucleating agents are typically present in an amount of less than about 0.5 wt. %, in some embodiments less than about 0.25 wt. %, and in some embodiments, less than about 0.1 wt. % of the second component.

Although aliphatic polyesters are the primary ingredient of the second component, other ingredients may of course be utilized the second component for a variety of different reasons. For instance, a wetting agent may be employed in some embodiments of the present invention to improve the hydrophilicity of the resulting fibers. Wetting agents suitable for use in the present invention are generally compatible with the aliphatic polyesters. Examples of suitable wetting agents may include surfactants, such as UNITHOX® 480 and UNITHOX® 750 ethoxylated alcohols, or UNICID™ acid amide ethoxylates, all available from Petrolite Corporation of Tulsa, Okla. Other suitable wetting agents are described in U.S. Pat. No. 6,177,193 to Tsai, et al., which is incorporated herein in its entirety by reference thereto for all relevant purposes. Still other materials that may be used include, without limitation, pigments, antioxidants, stabilizers, surfactants, waxes, flow promoters, solid solvents, plasticizers, particulates, and other materials added to enhance the processability of the thermoplastic composition. When utilized, it is normally desired that the amounts of these additional ingredients are minimized to ensure optimum compatibility and cost-effectiveness. Thus, for example, it is normally desired that such ingredients constitute less than about 10 wt. %, in some embodiments less than about 8 wt. %, and in some embodiments, less than about 5 wt. % of the second component.

III. Methods for Forming Multicomponent Fibers

Any of a variety of known techniques may be employed to form the multicomponent fibers of the present invention. Typically, the components are extruded in separate extruders, but they may also be spun together. Referring to FIG. 1, for example, one embodiment of a process 10 for forming multicomponent fibers in accordance with the present invention is shown. As illustrated, the process 10 of this embodiment is arranged to produce bicomponent fibers, although it should be understood that other embodiments are contemplated by the present invention. The process 10 employs a pair of extruders 12a and 12b for separately extruding a first component A (i.e., "high melting point" polymer component) and a second component B (i.e., "high melting point" polymer component). The relative amount of the components A and B may generally vary based on the desired properties. For example, the first component A may constitute from about 5 wt. % to about 95 wt. %, in some embodiments from about 10 wt. % to about 90 wt. %, and in some embodiments, from about 15 wt. % to about 85 wt. % of the multicomponent fibers. Likewise, the second component B may constitute from about 5 wt. % to about 95 wt. %, in some embodiments from about 10 wt. % to about 90 wt. %, and in some embodiments, from about 15 wt. % to about 85 wt. % of the multicomponent fibers.

The first component A is fed into the respective extruder 12a from a first hopper 14a and the second component B is fed into the respective extruder 12b from a second hopper 14b. The components A and B are fed from the extruders 12a and 12b through respective polymer conduits 16a and 16b to a spinneret 18. Spinnerets for extruding multicomponent fibers are well known to those of skill in the art. For example, the spinneret 18 may include a housing containing a spin pack having a plurality of plates stacked one on top of each other and having a pattern of openings arranged to create flow paths for directing polymer components A and B separately through the spinneret 18. The spinneret 18 also has openings arranged in one or more rows. The openings form a downwardly extruding curtain of fibers when the polymers are extruded therethrough. The spinneret 18 may be arranged to form sheath/core, side-by-side, pie, or other configurations.

The process 10 also employs a quench blower 20 positioned adjacent the curtain of fibers extending from the spinneret 18. Air from the quench air blower 20 quenches the fibers extending from the spinneret 18. The quench air may be directed from one side of the fiber curtain as shown in FIG. 1 or both sides of the fiber curtain. A fiber draw unit or aspirator 22 is positioned below the spinneret 18 and receives the quenched fibers. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255, which are incorporated herein in their entirety by reference thereto for all relevant purposes. The fiber draw unit 22 generally includes an elongate vertical passage through which the fibers are drawn by aspirating air entering from the sides of the passage and flowing downwardly through the passage. A heater or blower 24 supplies aspirating air to the fiber draw unit 22. The aspirating air draws the fibers and ambient air through the fiber draw unit 22. Thereafter, the fibers may be wound onto a godet roll assembly 42. Alternatively, the fibers may be directly formed into a coherent web structure by randomly depositing the fibers onto a forming surface (optionally with the aid of a vacuum) and then bonding the resulting web using any known technique.

To initiate fiber formation, the hoppers 14a and 14b are initially filled with the respective components A and B. Components A and B are melted and extruded by the respective extruders 12a and 12b through polymer conduits 16a and 16b and the spinneret 18. Due to the relatively low apparent viscosity of the aliphatic polyesters used in the present invention, lower extrusion temperatures may be employed. For example, the extruder 12b for Component B ("low melting point" polyester) may employ one or multiple zones operating at a temperature of from about 120° C. to about 200° C., and in some embodiments, from about 145° C. to about 195° C. Likewise, the extruder 12a for Component A ("high melting point" polyester) may employ one or multiple zones operating at a temperature of from about 160° C. to about 250° C., and in some embodiments, from about 190° C. to about 225° C. Typical shear rates range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$.

As the extruded fibers extend below the spinneret 18, a stream of air from the quench blower 20 at least partially quenches the fibers. Such a process generally reduces the temperature of the extruded polymers at least about 100° C. over a relatively short time frame (seconds). This will generally reduce the temperature change needed upon cooling, to preferably be less than 150° C. and, in some cases, less than 100° C. The ability to use relatively low extruder temperature in the present invention also allows for the use of lower quenching temperatures. For example, the quench blower 20 may employ one or more zones operating at a temperature of from about 20° C. to about 100° C., and in some embodiments, from about 25° C. to about 60° C. After quenching, the fibers are drawn into the vertical passage of the fiber draw unit 22 by a flow of a gas such as air, from the heater or blower 24 through the fiber draw unit. The flow of gas causes the fibers to draw or attenuate which increases the molecular orientation or crystallinity of the polymers forming the fibers. The fibers are deposited through the outlet opening of the fiber draw unit 22 and onto the godet roll assembly 42. Due to the high strength of the fibers of the present invention, high draw ratios (e.g., speed of the godet roll 42 divided by the melt pump rate of the extruders 12a and 12b) may be achieved in the present invention. For example, the draw ratio may be from about 200:1 to about 6000:1, in some embodiments from about 500:1 to about 5000:1, and in some embodiments, from about 1000:1 to about 4000:1. Alternatively, the fibers may be deposited directly onto a foraminous surface (not shown) to directly form a nonwoven web.

If desired, the fibers collected on the godet roll 42 may optionally be subjected to additional in line processing and/or converting steps (not shown) as will be understood by those skilled in the art. For example, staple fibers may be formed by "cold drawing" the collected fibers at a temperature below their softening temperature to the desired diameter, and thereafter crimping, texturizing, and/or and cutting the fibers to the desired fiber length. The desired fiber length and denier of the fibers may vary depending on the desired application. Typically, the fibers are formed to have an average fiber length in the range of from about 3 to about 80 millimeters, in some embodiments from about 4 to about 65 millimeters, and in some embodiments, from about 5 to about 50 millimeters. The denier per filament of the fibers may also be less than about 6, in some embodiments less than about 3, and in some embodiments, from about 0.5 to about 3. In addition, the fibers are generally "microfibers", i.e., small diameter fibers having an average diameter not greater than about 100 microns, in some embodiments from about 0.5 microns to about 50 microns, and in some embodiments, from about 4 microns to about 40 microns.

Various other methods for forming multicomponent fibers may also be used in the present invention, such as described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Regardless of the particular manner in which they are formed, the present inventors have discovered that the resulting multicomponent fibers exhibit excellent strength characteristics. One parameter that is indicative of the relative strength of the multicomponent fibers of the present invention is "tenacity", which indicates the tensile strength of a fiber expressed as force per unit linear density. For example, the multicomponent fibers of the present invention may have a tenacity of from about 0.75 to about 7.0 grams-force ("$g_f$") per denier, in some embodiments from about 1.0 to about 5.0 $g_f$ per denier, and in some embodiments, from about 1.5 to about 4.0 $g_f$ per denier. Furthermore, the multicomponent fibers of the present invention also have a relatively high "peak tensile stress", which indicates the maximum tensile stress expressed in force per unit area. For example, the multicomponent fibers of the present invention may have a peak tensile stress of from about 100 to about 600 Megapascals (MPa), in some embodiments from about 150 to about 500 MPa, and in some embodiments, from about 200 to about 400 MPa.

IV. Nonwoven Webs

The multicomponent fibers of the present invention may be employed in any type of nonwoven web, such as a meltblown web, spunbond web, bonded carded web, wet-laid web, airlaid web, coform web, hydraulically entangled web, etc. In one embodiment, for example, the fibers are formed into a carded web by placing bales of fibers into a picker that separates the fibers. Next, the fibers are sent through a combing or carding unit that further breaks apart and aligns the fibers in the machine direction so as to form a machine direction-oriented fibrous nonwoven web. Once formed, the nonwoven web is typically stabilized by one or more bonding techniques. For example, a through-air dryer containing one or more heating zones may be employed that heats air to a temperature greater than the melting temperature of the second component (e.g., sheath) of the multi-component fibers, but less than the melting temperature of the first component (e.g., core). This heated air passes though the nonwoven web, thereby melting the second component and forming interfiber bonds to thermally stabilize the web. When polylactic acid and polybutylene succinate are used as polymer components, for example, the air flowing through the through air bonder may have a temperature ranging from about 100° C. to about 180° C. The dwell time in the through air bonder may also be about 120 seconds or less. It should be understood, however, that the parameters of the through air bonder depend on factors such as the type of polymers used and thickness of the web.

Ultrasonic bonding techniques may also be used that employ a stationary or rotary horn and a rotating patterned anvil roll. Such techniques are described in U.S. Pat. No. 3,939,033 to Grgach, et al.; U.S. Pat. No. 3,844,869 to Rust Jr.; U.S. Pat. No. 4,259,399 to Hill, U.S. Pat. No. 5,096,532 to Neuwirth, et al., U.S. Pat. No. 5,110,403 to Ehlert, and U.S. Pat. No. 5,817,199 to Brennecke, et al., which are incorporated herein in their entirety by reference thereto for all purposes. Alternatively, the nonwoven web may be thermally point bonded to provide a fabric having numerous small, discrete bond points. This process generally involves passing the web between heated rolls, such as an engraved patterned roll and a second bonding roll. The engraved roll is patterned in some way so that the web is not bonded over its entire surface, and the second roll may be smooth or patterned. Various patterns for engraved rolls have been developed for functional and/or aesthetic reasons. Exemplary bond patterns include, but are not limited to, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown, which are incorporated herein in their entirety by reference thereto for all purposes. For instance, the nonwoven web may be bonded to have a total bond area of less than about 30 percent and a uniform bond density greater than about 100 bonds per square inch, and preferably from about 2 to about 30 percent (as determined by conventional optical microscopic methods) and a bond density from about 250 to about 500 pin bonds per square inch. Such a combination of total bond area and bond density may be achieved by bonding the web with a pin bond pattern having more than about 100 pin bonds per square inch that provides a total bond surface area less than about 30 percent when fully contacting a smooth anvil roll. In some embodiments, the bond pattern may have a pin bond density from about 250 to about 350 pin bonds per square inch and a total bond surface area from about 10 percent to about 25 percent when contacting a smooth anvil roll.

The multicomponent fibers may constitute the entire fibrous component of the nonwoven web or blended with other types of fibers. When blended with other types of fibers, it is normally desired that the multicomponent fibers of the present invention constitute from about 0.5 wt % to about 60 wt. %, in some embodiments from about 1 wt. % to about 40 wt. %, and in some embodiments, from about 2 wt. % to about 20 wt. % of the total amount of fibers employed in the nonwoven web.

For example, the multicomponent fibers of the present invention may be blended with pulp fibers, such as high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Wash. under the trade designation of "NB-416." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability. Typically, pulp fibers constitute from about 30 wt. % to about 95 wt. %, in some embodiments from about 40 wt. % to about 90 wt. %, and in some embodiments, from about 50 wt. % to about 85 wt. % of the nonwoven web.

Additional monocomponent and/or multicomponent synthetic fibers may also be utilized in the nonwoven web. Some suitable polymers that may be used to form the synthetic fibers include, but are not limited to: polyolefins, e.g., polyethylene, polypropylene, polybutylene, and the like; polytetrafluoroethylene; polyesters, e.g., polyethylene terephthalate and the like; polyvinyl acetate; polyvinyl chloride acetate; polyvinyl butyral; acrylic resins, e.g., polyacrylate, polymethylacrylate, polymethylmethacrylate, and the like; polyamides, e.g., nylon; polyvinyl chloride; polyvinylidene chloride; polystyrene; polyvinyl alcohol; polyurethanes; polylactic acid; and the like. If desired, biodegradable polymers, such as poly(glycolic acid) (PGA), poly(lactic acid) (PLA), poly(β-malic acid) (PMLA), poly(ε-caprolactone) (PCL), poly(p-dioxanone) (PDS), and poly(3-hydroxybutyrate) (PHB). Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. Nonwood fibers may also be used, including fiber originating from hemp, straw, flax, bagasse, and mixtures thereof may be used in the present invention.

Further, superabsorbent materials may also be contained within the nonwoven web. Superabsorbent materials are water-swellable materials capable of absorbing at least about 20 times its weight and, in some cases, at least about 30 times its weight in an aqueous solution containing 0.9 weight percent sodium chloride. The superabsorbent materials may be natural, synthetic and modified natural polymers and materials. Examples of synthetic superabsorbent polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Other superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Particularly suitable superabsorbent polymers are HYSORB 8800AD (BASF of Charlotte, N.C. and FAVOR SXM 9300 (available from Degussa Superabsorber of Greensboro, N.C.). When utilized, the superabsorbent material may constitute from about 30 wt. % to about 95 wt. %, in some embodiments from about 40 wt. % to about 90 wt. %, and in some embodiments, from about 50 wt. % to about 85 wt. % of the nonwoven web.

V. Absorbent Articles

Nonwoven webs, such as described above, may be used in an absorbent article, such as, but not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. The nonwoven web of the present invention may be employed as any one or more of the liquid-permeable, liquid-impermeable, and/or absorbent layers.

Figure 5:
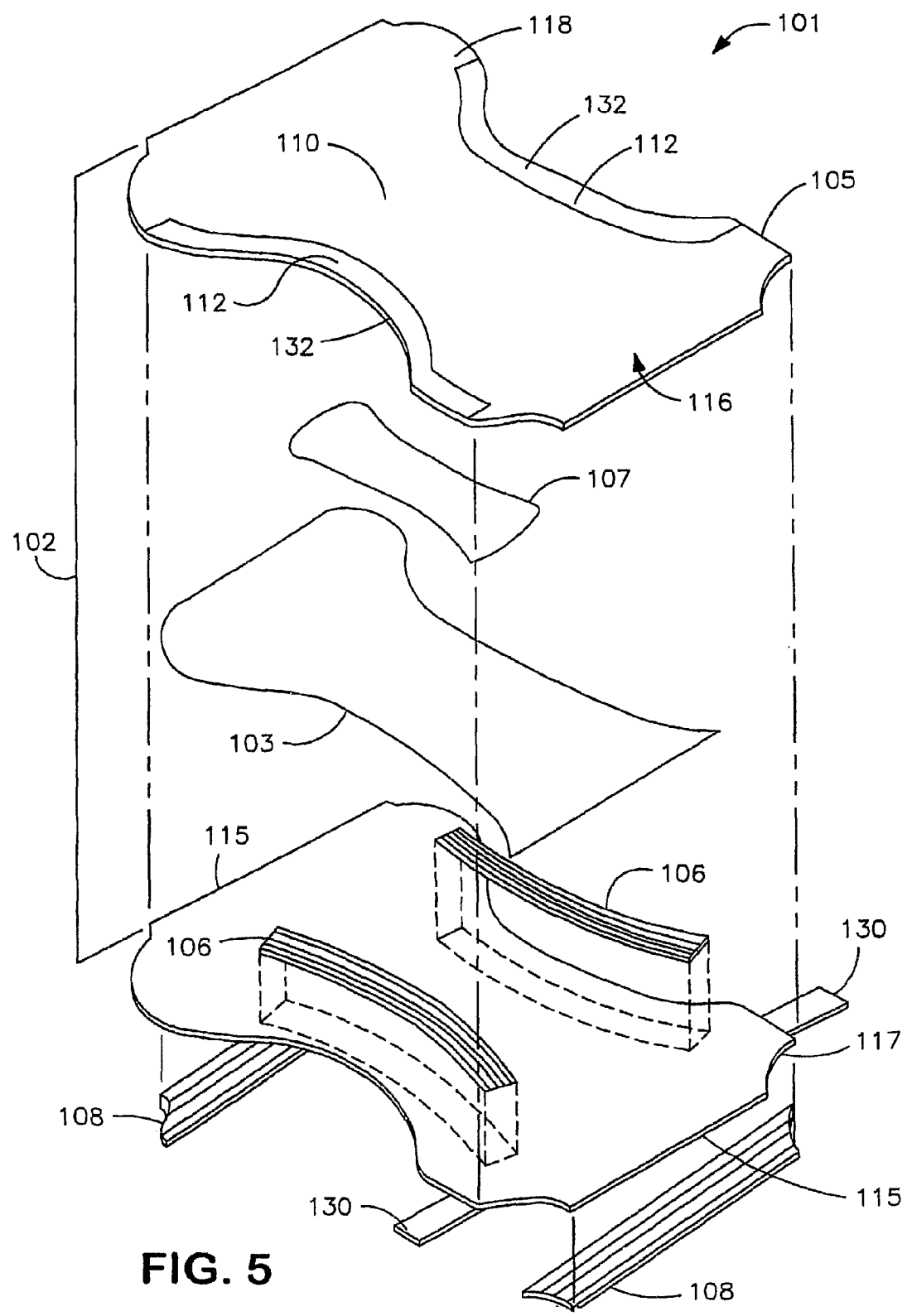
FIG. 5 is a perspective view of an absorbent article that may be formed according to one embodiment of the present invention.

Various embodiments of an absorbent article that may be formed according to the present invention will now be described in more detail. For purposes of illustration only, an absorbent article is shown in FIG. 5 as a diaper 101. However, as noted above, the invention may be embodied in other types of absorbent articles, such as incontinence articles, sanitary napkins, diaper pants, feminine napkins, children's training pants, and so forth. In the illustrated embodiment, the diaper 101 is shown as having an hourglass shape in an unfastened configuration. However, other shapes may of course be utilized, such as a generally rectangular shape, T-shape, or I-shape. As shown, the diaper 101 includes a chassis 102 formed by various components, including an outer cover 117, bodyside liner 105, absorbent core 103, and surge layer 107. It should be understood, however, that other layers may also be used in the present invention. Likewise, one or more of the layers referred to in FIG. 5 may also be eliminated in certain embodiments of the present invention.

The outer cover 117 is typically formed from a material that is substantially impermeable to liquids. For example, the outer cover 117 may be formed from a thin plastic film or other flexible liquid-impermeable material. In one embodiment, the outer cover 117 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 may be formed from a polyolefin film laminated to a nonwoven web. For example, a stretch-thinned polypropylene film having a thickness of about 0.015 millimeter may be thermally laminated to a spunbond web of polypropylene fibers. If desired, the nonwoven web may contain the multicomponent fibers of the present invention.

The diaper 101 also includes a bodyside liner 105. The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. The liner 105 may be liquid-permeable to permit liquid to readily penetrate through its thickness. In one particular embodiment, the liner includes a nonwoven web (e.g., spunbond web, meltblown web, or bonded carded web) containing the multicomponent fibers of the present invention. Exemplary liner constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941, all of which are incorporated herein in their entirety by reference thereto for all purposes.

As illustrated in FIG. 5, the diaper 101 may also include a surge layer 107 that helps to decelerate and diffuse surges or gushes of liquid that may be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 may be located on an outwardly facing surface 118 of the bodyside liner 105. The surge layer 107 is typically constructed from highly liquid-permeable materials. Suitable materials may include porous woven materials, porous nonwoven materials, and apertured films. In one particular embodiment, the surge layer 107 includes a nonwoven web containing the multicomponent fibers of the present invention. Other examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

Besides the above-mentioned components, the diaper 101 may also contain various other components as is known in the art. For example, the diaper 101 may also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 103. The wrapsheet material on one side of the absorbent fibrous mass may be bonded to the wrapsheet located on the opposite side of the fibrous mass to effectively entrap the absorbent core 103. If desired, the wrapsheet may be formed from a nonwoven web that includes the multicomponent fibers of the present invention.

Furthermore, the diaper 101 may also include a ventilation layer (not shown) that is positioned between the absorbent core 103 and the outer cover 117. When utilized, the ventilation layer may help insulate the outer cover 117 from the absorbent core 103, thereby reducing dampness in the outer cover 117. Examples of such ventilation layers may include a nonwoven web laminated to a breathable film, such as described in U.S. Pat. No. 6,663,611 to Blaney, et al., which is incorporated herein in its entirety by reference thereto for all purpose. Such nonwoven webs may be formed from a nonwoven web that includes the multicomponent fibers of the present invention.

In some embodiments, the diaper 101 may also include a pair of ears (not shown) that extend from the side edges 132 of the diaper 101 into one of the waist regions. The ears may be integrally formed with a selected diaper component. For example, the ears may be integrally formed with the outer cover 117 or from the material employed to provide the top surface. In alternative configurations, the ears may be provided by members connected and assembled to the outer cover 117, the top surface, between the outer cover 117 and top surface, or in various other configurations.

As representatively illustrated in FIG. 5, the diaper 101 may also include a pair of containment flaps 112 that are configured to provide a barrier and to contain the lateral flow of body exudates. The containment flaps 112 may be located along the laterally opposed side edges 132 of the bodyside liner 105 adjacent the side edges of the absorbent core 103. The containment flaps 112 may extend longitudinally along the entire length of the absorbent core 103, or may only extend partially along the length of the absorbent core 103. When the containment flaps 112 are shorter in length than the absorbent core 103, they may be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704, 116 to Enloe, which is incorporated herein in its entirety by reference thereto for all purposes.

The diaper 101 may include various elastic or stretchable materials, such as a pair of leg elastic members 106 affixed to the side edges 132 to further prevent leakage of body exudates and to support the absorbent core 103. In addition, a pair of waist elastic members 108 may be affixed to longitudinally opposed waist edges 115 of the diaper 101. The leg elastic members 106 and the waist elastic members 108 are generally adapted to closely fit about the legs and waist of the wearer in use to maintain a positive, contacting relationship with the wearer and to effectively reduce or eliminate the leakage of body exudates from the diaper 101. As used herein, the terms "elastic" and "stretchable" include any material that may be stretched and return to its original shape when relaxed. Suitable polymers for forming such materials include, but are not limited to, block copolymers of polystyrene, polyisoprene and polybutadiene; copolymers of ethylene, natural rubbers and urethanes; etc. Particularly suitable are styrene-butadiene block copolymers sold by Kraton Polymers of Houston, Tex. under the trade name Kraton®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels.

The diaper 101 may also include one or more fasteners 130. For example, two flexible fasteners 130 are illustrated in FIG. 5 on opposite side edges of waist regions to create a waist opening and a pair of leg openings about the wearer. The shape of the fasteners 130 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 130 includes a separate piece of hook material affixed to the inside surface of a flexible backing.

The various regions and/or components of the diaper 101 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 may be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, may also be assembled into the diaper 101 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes.

The present invention may be better understood with reference to the following examples.

Test Methods

Molecular Weight:

The molecular weight distribution of a polymer was determined by gel permeation chromatography ("GPC"). The samples were initially prepared by adding 0.5% wt/v solutions of the sample polymers in chloroform to 40-milliliter glass vials. For example, 0.05±0.0005 grams of the polymer was added to 10 milliliters of chloroform. The prepared samples were placed on an orbital shaker and agitated overnight. The dissolved sample was filtered through a 0.45-micron PTFE membrane and analyzed using the following conditions:

Columns: Styragel HR 1, 2, 3, 4, & 5E (5 in series) at 41° C.
Solvent/Eluent: Chloroform @1.0 milliliter per minute
HPLC: Waters 600E gradient pump and controller, Waters 717 auto sampler
Detector: Waters 2414 Differential Refractometer at sensitivity=30, at 40° C. and scale factor of 20
Sample Concentration: 0.5% of polymer "as is"
Injection Volume: 50 microliters
Calibration Standards Narrow MW polystyrene, 30-microliter injected volume.

Number Average Molecular Weight ($MW_n$), Weight Average Molecular Weight ($MW_w$) and first moment of viscosity average molecular weight ($MW_z$) were obtained.

Apparent Viscosity:

The rheological properties of polymer samples were determined using a Göttfert Rheograph 2003 capillary rheometer with WinRHEO version 2.31 analysis software. The setup included a 2000-bar pressure transducer and a 30/1:0/180 roundhole capillary die. Sample loading was done by alternating between sample addition and packing with a ramrod. A 2-minute melt time preceded each test to allow the polymer to completely melt at the test temperature (usually 160 to 220° C.). The capillary rheometer determined the apparent viscosity (Pa·s) at seven different shear rates: 50, 100, 200, 500, 1000, 2000 and 5000 s$^{-1}$. The resultant rheology curve of apparent shear rate versus apparent viscosity gave an indication of how the polymer would run at that temperature in an extrusion process.

Melt Flow Index:

The melt flow index is the weight of a polymer (in grams) forced through an extrusion rheometer orifice (0.0825-inch diameter) when subjected to a force of 2160 grams in 10 minutes at 190° C. The melt flow index was measured in accordance with ASTM Test Method D1238-E.

Thermal Properties: (melting point, $T_g$, and % crystallinity):

The melting temperature, glass transition temperature and degree of crystallinity of a material was determined by differential scanning calorimetry (DSC). The differential scanning calorimeter was a THERMAL ANALYST 2910 Differential Scanning Calorimeter, which was outfitted with a liquid nitrogen cooling accessory and with a THERMAL ANALYST 2200 (version 8.10) analysis software program, both of which are available from T.A. Instruments Inc. of New Castle, Del. To avoid directly handling the samples, tweezers or other tools were used. The samples were placed into an aluminum pan and weighed to an accuracy of 0.01 milligram on an analytical balance. A lid was crimped over the material sample onto the pan. Typically, the resin pellets were placed directly in the weighing pan, and the fibers were cut to accommodate placement on the weighing pan and covering by the lid.

The differential scanning calorimeter was calibrated using an indium metal standard and a baseline correction was performed, as described in the operating manual for the differential scanning calorimeter. A material sample was placed into the test chamber of the differential scanning calorimeter for testing, and an empty pan is used as a reference. All testing was run with a 55-cubic centimeter per minute nitrogen (industrial grade) purge on the test chamber. For resin pellet samples, the heating and cooling program was a 2-cycle test that began with an equilibration of the chamber to −25° C., followed by a first heating period at a heating rate of 10° C.

per minute to a temperature of 200° C., followed by equilibration of the sample at 200° C. for 3 minutes, followed by a first cooling period at a cooling rate of 20° C. per minute to a temperature of −25° C., followed by equilibration of the sample at −25° C. for 3 minutes, and then a second heating period at a heating rate of 10° C. per minute to a temperature of 200° C. For fiber samples, the heating and cooling program was a 1-cycle test that began with an equilibration of the chamber to −25° C., followed by a heating period at a heating rate of 20° C. per minute to a temperature of 200° C., followed by equilibration of the sample at 200° C. for 3 minutes, and then a cooling period at a cooling rate of 10° C. per minute to a temperature of −25° C. All testing was run with a 55-cubic centimeter per minute nitrogen (industrial grade) purge on the test chamber.

The results were then evaluated using the THERMAL ANALYST 2200 analysis software program, which identified and quantified the glass transition temperature ($T_g$) of inflection, the endothermic and exothermic peaks, and the areas under the peaks on the DSC plots. The glass transition temperature was identified as the region on the plot-line where a distinct change in slope occurred, and the melting temperature was determined using an automatic inflection calculation. The areas under the peaks on the DSC plots were determined in terms of joules per gram of sample (J/g). For example, the endothermic heat of melting of a resin or fiber sample was determined by integrating the area of the endothermic peak. The area values were determined by converting the areas under the DSC plots (e.g. the area of the endotherm) into the units of joules per gram (J/g) using computer software. The % crystallinity was calculated as follows:

$$\% \text{ crystallinity} = 100*(A-B)/C$$

wherein,

A is the sum of endothermic peak areas (J/g);

B is the sum of exothermic peak areas (J/g); and

C is the endothermic heat of melting value for the selected polymer where such polymer has 100% crystallinity (J/g). For polylactic acid, C is 93.7 J/g (Cooper-White, J. J., and Mackay, M. E., *Journal of Polymer Science*, Polymer Physics Edition, p. 1806, Vol. 37, (1999)). The areas under any exothermic peaks encountered in the DSC scan due to insufficient crystallinity were subtracted from the area under the endothermic peak to appropriately represent the degree of crystallinity.

Tensile Properties:

The Strip tensile strength values were determined in substantial accordance with ASTM Standard D-5034. Specifically, a nonwoven web sample was cut or otherwise provided with size dimensions that measure 25 millimeters (width)× 127 millimeters (length). A constant-rate-of-extension type of tensile tester was employed. The tensile testing system was a MTS SYNERGY 200 Tensile Tester, which is available from MTS Systems Corporation of Eden Prairie, Mich. The tensile tester was equipped with TESTWORKS 4.08B software from MTS Corporation to support the testing. An appropriate load cell was selected so that the tested value fell within the range of 10-90% of the full scale load. The sample was held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run at a 300-millimeter per minute rate with a gauge length of 76 millimeters and a break sensitivity of 40%.

Three samples were tested by applying the test load along the machine-direction and three samples were tested by applying the test load along the cross direction. In addition to tensile strength, the peak load, peak stretch (i.e., % elongation at peak load), and the energy to peak was measured. The peak strip tensile loads from each specimen tested were arithmetically averaged to determine the MD or CD tensile strength.

Fiber Tenacity:

Individual fiber specimens were carefully extracted from an unbonded portion of a fiber web in a manner that did not significantly pull on the fibers. These fiber specimens were shortened (e.g. cut with scissors) to 38 millimeters in length, and placed separately on a black velvet cloth. 10 to 15 fiber specimens were collected in this manner. The fiber specimens were then mounted in a substantially straight condition on a rectangular paper frame having external dimension of 51 millimeters×51 millimeters and internal dimension of 25 millimeters×25 millimeters. The ends of each fiber specimen were operatively attached to the frame by carefully securing the fiber ends to the sides of the frame with adhesive tape. Each fiber specimen was then be measured for its external, relatively shorter, cross-fiber dimension employing a conventional laboratory microscope, which has been properly calibrated and set at 40× magnification. This cross-fiber dimension was recorded as the diameter of the individual fiber specimen. The frame helped to mount the ends of the sample fiber specimens in the upper and lower grips of a constant rate of extension type tensile tester in a manner that avoided excessive damage to the fiber specimens.

A constant rate of extension type of tensile tester and an appropriate load cell were employed for the testing. The load cell was chosen (e.g. 10N) so that the test value fell within 10-90% of the full scale load. The tensile tester (i.e., MTS SYNERGY 200) and load cell were obtained from MTS Systems Corporation of Eden Prairie, Mich. The fiber specimens in the frame assembly were then mounted between the grips of the tensile tester such that the ends of the fibers were operatively held by the grips of the tensile tester. Then, the sides of the paper frame that extended parallel to the fiber length were cut or otherwise separated so that the tensile tester applied the test force only to the fibers. The fibers were then subjected to a pull test at a pull rate and grip speed of 12 inches per minute. The resulting data was analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | Break threshold | 10 $g_f$ |
| Nominal gage length | 1 in | Data Acq. Rate | 10 Hz |
| Slack pre-load | 1 $lb_f$ | Denier length | 9000 m |
| Slope segment length | 20% | Density | 1.25 g/cm$^3$ |
| Yield offset | 0.20% | Initial speed | 12 in/min |
| Yield segment length | 2% | Secondary speed | 2 in/min |

The tenacity values were expressed in terms of gram-force per denier.

Example 1

Various physical properties of the following aliphatic polyesters were tested.

P1: Polybutylene succinate obtained from IRE Chemicals, South Korea under the name EnPol™ G4500 (Grade CE272);

P2: Polybutylene succinate obtained from IRE Chemicals, South Korea under the name EnPol™ G4500 (Grade 1DF241);

P3: Polybutylene succinate obtained from IRE Chemicals, South Korea under the name EnPol™ G4500 (Grade 2DF242);

P4: Polybutylene succinate obtained from IRE Chemicals, South Korea under the name EnPol™ G4560J;

P5: Polybutylene succinate obtained from IRE Chemicals, South Korea under the name EnPol™ G4500 (Grade CE272—High MFI);

P6: Polybutylene succinate obtained from IRE Chemicals, South Korea under the name EnPol™ G4500 (Grade CE272—Mid MFI);

P7: Polybutylene succinate obtained from Showa, Japan under the name Bionolle™ 1020;

P8: Polybutylene succinate obtained from Showa, Japan under the name Bionolle™ 1903;

P9: Polybutylene succinate obtained from Showa, Japan under the name Bionolle™ 1003; and P10: Polylactic acid obtained from Biomer Inc., Germany under the name Biomer™ L9000.

The results are set forth below in Tables 1 and 2.

extruders each were single screw type and had five separately controlled heating zones. The melt pump was a positive displacement type pump whose throughput (cc/sec) was controlled through its speed (rpm). The extruder throughput was automatically controlled by the throughput demand of the melt pump. The molten polymer from the pump was fed into the heated spin pack assembly having 16 holes of 0.4 or 0.6 millimeters in size. The spin pack assembly contained a spin plate and channeling plates (32 channels) that kept the two polymer streams separate until reaching the spin plate. The extruded polymers were in the form of strands, which were annealed or quenched by a hot or cold air supply through a 1.5-meter long spinning chamber. The fiber strands were subsequently pulled fast and collected on a godet roll. After a fixed amount of time, the godet roll was stopped and the fibers were collected. These fibers were then subjected to analysis and compared to commercially available fibers. The results are set forth below in Tables 3-7.

TABLE 1

Molecular Weight and Melt Properties

| Polymer | $MW_n$ | $MW_w$ | Polydispersity Index | Melt Flow Index (190° C., 2.16 kg) | Melt Temp (° C.) | Heat of Fusion, (J/g) | Crystallization Temp. (° C.) | Heat of Crystallization (J/g) |
|---|---|---|---|---|---|---|---|---|
| P1 | 78,000 | 126,900 | 1.63 | 47 | 114.95 | 49.45 | 79.08 | 57.86 |
| P2 | 59,500 | 99,200 | 1.67 | 150 | 114.94 | 64.26 | 70.86 | 62.38 |
| P3 | 72,300 | 122,900 | 1.70 | 41 | 115.03 | 59.69 | 75.13 | 61.26 |
| P4 | 77,600 | 142,900 | 1.84 | 25 | 114.40 | — | — | — |
| P5 | 49,900 | 92,400 | 1.85 | 127 | 113.21 | 71.48 | 64.90 | 72.34 |
| P6 | 61,500 | 105,400 | 1.71 | 56 | 114.06 | 58.54 | 68.02 | 61.25 |
| P7 | — | — | — | 28 | 114.28 | 56.88 | 76.36 | 64.13 |
| P8 | — | — | — | — | — | — | — | — |
| P9 | — | — | — | 4.4 | — | — | — | — |
| P10 | 113.5 | 150.7 | 1.33 | 22 (210° C.) 43 (230° C.) | 169.60 | 3.70 | 71.38 | 33.46 |

TABLE 2

Rheological Properties (30/1/180 Roundhole)

| Apparent Shear Rate ($sec^{-1}$) | Apparent Viscosity (Pa-s) (at 160° C.) | | | | | | Apparent Viscosity (Pa-s) (at 220° C.) | | |
|---|---|---|---|---|---|---|---|---|---|
| | P4 | P2 | P3 | P7 | P8 | P9 | P4 | P10 | P3 |
| 50 | 407.1 | — | — | — | — | — | 65.1 | — | 98.0 |
| 100 | 325.7 | — | — | — | — | — | 48.9 | — | 73.3 |
| 200 | 268.7 | 86.0 | 212 | 395 | 578 | 973 | 44.8 | — | 73.3 |
| 500 | 192.2 | 76.0 | 163 | 293 | 360 | 621 | 44.0 | 261.0 | 63.5 |
| 1000 | 141.7 | 66.0 | 129 | 217 | 241 | 416 | 39.0 | 195.4 | 44.8 |
| 2000 | — | 53.3 | 95.3 | 148 | 157 | 248 | — | 179.0 | — |
| 5000 | — | 37.0 | 57 | 80.8 | 86.8 | — | — | 168.0 | — |

As indicated, the Bionolle™ polymers (P7-P9) were quite viscous compared to the EnPol™ G4500 polymers (P2-P4).

Example 2

Various polybutylene succinate polymers were dried at 160° F. and a polylactic acid polymer was dried at 175° F., both for at least 48 hours. The target moisture level was 50 ppm. The polymers were then fed through sealed hoppers into extruders that fed molten polymer to the melt pump. The

TABLE 3

Polymer Configuration

| Sample | Polymer 1 | Polymer 2 | Configuration (½) |
|---|---|---|---|
| 1 | P6 | P10 | Sheath (50%)/Core (50%) |
| 2 | P5 | P10 | Sheath (50%)/Core (50%) |
| 3 | P5 | — | Mono |
| 4 | P1 | — | Mono |
| 5 | P1 | EcoPla 6201* | Sheath (50%)/Core (50%) |
| 6 | P6 | EcoPla 6201* | Sheath (50%)/Core (50%) |
| 7 | P1 | — | Mono |
| 8 | P1 | P10 | Sheath (50%)/Core (50%) |
| 9 | P6 | — | Mono |
| 10 | P1 | EcoPla 6201* | Sheath (50%)/Core (50%) |
| 11 | P2 | P10 | Sheath (50%)/Core (50%) |
| 12 | P3 | P10 | Sheath (50%)/Core (50%) |
| 13 | P2 | P10 | Sheath (50%)/Core (50%) |
| 14 | P3 | P10 | Side (50%) – Side (50%) |
| 15 | P3 | P10 | Side (50%) – Side (50%) |
| 16 | P3 | P10 | Side (50%) – Side (50%) |
| 17 | P2 | — | Mono |
| 18 | P2 | P2 | Side (50%) – Side (50%) |
| 19 | P2 | P2 | Mono |
| 20 | P2 | P10 | Side (50%) – Side (50%) |
| 21 | P10 | — | Mono |
| 22 | P9 | — | Mono |
| 23 | P7 | — | Mono |
| 24 | P7 | P10 | Mono |
| 25 | PP 3155+ | — | Mono |

TABLE 3-continued

Polymer Configuration

| Sample | Polymer 1 | Polymer 2 | Configuration (½) |
|---|---|---|---|
| 26 | P10 | — | Mono |
| 27 | P10 | P3 | Core (93%)/Sheath (7%) |
| 28 | P10 | P3 | Core (85%)/Sheath (10%) |
| 29 | P10 | P3 | Core (70%)/Sheath (30%) |
| 30 | P10 | P2 | Core (93%)/Sheath (7%) |
| 31 | P10 | P2 | Core (70%)/Sheath (30%) |

*Polylactic acid available from Natureworks LLC.
†Isotactic homopolypropylene available from Exxon Mobil Chemical Co.

TABLE 4

Extrusion Conditions

| Sample | Moisture (ppm) Polymer 1/Polymer 2 | Extruder 1 Profile 1/2/3/4/5 zone (°C.) | Extruder 2 Profile 1/2/3/4/5 zone (°C.) | Spin Pack Temp (°C.) | Hole diameter (mm) |
|---|---|---|---|---|---|
| 1 | 135/165 | 165/170/170/175/175/175/175 | 190/210/21/210/210/210/210 | 222 | 0.6 |
| 2 | 105/165 | 165/170/170/175/175/175/175 | 190/210/210/210/210/210/210 | 222 | 0.6 |
| 3 | 105 | 145/145/145/148/148/150/150 | — | 170 | 0.6 |
| 4 | 58 | 170/170/170/175/175/180/180 | — | 185 | 0.6 |
| 5 | 79/72 | 180/180/185/190/195/195/195 | 190/215/215/215/225/225/225 | 240 | 0.4 |
| 6 | 117/72 | 180/180/185/190/195/195/195 | 190/215/215/215/225/225/225 | 240 | 0.4 |
| 7 | 79 | 170/170/175/175/180/180/180 | — | 185 | 0.4 |
| 8 | 79 | 175/185/195/195/195/195/195 | 190/215/215/215/225/225/225 | 225 | 0.4 |
| 9 | 83 | 160/160/165/170/170/170/170 | — | 180 | 0.4 |
| 10 | — | 168/175/180/185/185/185/185 | 200/225/225/230/232/232/235 | 235 | 0.4 |
| 11 | 33/22 | 165/165/165/165/165/165/165 | 200/205/207/207/210/210/210 | 225 | 0.6 |
| 12 | 27/75 | 165/170/170/173/173/175/175 | 190/210210/210/210/215/215 | 220 | 0.6 |
| 13 | 33/75 | 155/160/160/163/163/165/165 | 190/210210/210/210/215/215 | 220 | 0.6 |
| 14 | 82/32 | 170/170/170/175/175/175/175 | 200/200207/207/210/210/210 | 225 | 0.6 |
| 15 | 82/32 | 170/170/170/175/175/175/175 | 200/200207/207/210/210/210 | 230 | 0.6 |
| 16 | 82/32 | 170/170/170/175/175/175/175 | 200/200207/207/210/210/210 | 230 | 0.6 |
| 17 | NR/NR | 160/160/160/165/165/165/165 | 160/160/160/165/165/165/165 | 180 | 0.6 |
| 18 | 20/NR | 170/170/170/175/175/175/175 | 170/170/170/175/175/175/175 | 180 | 0.6 |
| 19 | 20/20 | 170/170/170/175/175/175/175 | 170/170/170/175/175/175/175 | 180 | 0.6 |
| 20 | 22/32 | 165/165/165/165/165/165/165 | 200/207/207/207/207/210/210 | 225 | 0.6 |
| 21 | 45 | 190/190/210/210/220/225/230 | — | 250 | 0.6 |
| 22 | 92 | 210/210/215/220/222/227/230 | — | 230 | 0.6 |
| 23 | 140 | 210/210/215/220/222/227/230 | — | 230 | 0.6 |
| 24 | 140/45 | 175/185/210/215/218/220/220 | 200/200/205/210/210/215/215 | 220 | 0.6 |
| 25 | — | — | — | 247 | 0.6 |
| 26 | — | 190/190/210/210/220/225/230 | — | 250 | 0.6 |
| 27 | — | 180/190/190/200/200/210/210 | 185/200/210/215/215/220/220 | 240 | 0.6 |
| 28 | — | 180/190/190/200/200/210/210 | 185/200/210/215/215/220/220 | 240 | 0.6 |
| 29 | — | 180/190/190/200/200/210/210 | 195/205/215/220/220/225/225 | 240 | 0.6 |
| 30 | — | 180/190/190/200/200/210/210 | 195/205/215/220/220/225/225 | 240 | 0.6 |
| 31 | — | 175/185/185/195/195/205/205 | 195/205/215/220/220/225/225 | 235 | 0.6 |

| Sample | Melt Pump Rate (rpm) Pump 1/Pump 2 | Melt Pump Outlet Pressure (psi) Pump 1/Pump 2 | Air Temp (°C.) 1/2/3/4 | Air Flow (CFM) Upper/Lower | Godet Roll Speed (m/min) | Draw Ratio | GHM |
|---|---|---|---|---|---|---|---|
| 1 | 5.0/5.0 | 250/305 | 27/26/25/24 | 2/21 | 1800 | 1394 | 0.40 |
| 2 | 5.0/5.0 | 185/250 | 59/40/33/26 | 410/393 | 2200 | 1700 | 0.40 |
| 3 | 5.0 | — | 31/30/27/24 | 0/0 | 2000 | 3100 | 0.20 |
| 4 | 5.0 | — | — | — | 200 | 300 | 0.20 |
| 5 | 5.0/5.0 | 405/275 | 109/47/28/24 | 270/250 | 2000 | 690 | 0.40 |
| 6 | 5.0/5.0 | 390/300 | 109/47/28/24 | 270/250 | 1800 | 620 | 0.40 |
| 7 | 5.0 | 535 | 25/25/25/24 | 305/260 | 500 | 344 | 0.20 |
| 8 | 3.0/3.0 | — | 84/NR/NR/NR/NR | | 2000 | 1150 | 0.24 |
| 9 | 5.0 | 865 | 35/35/34/24 | 220/0 | 350 | 241 | 0.20 |
| 10 | 2.5/2.5 | 65/155 | 55/32/31/27 | 460/425 | Up to 2000 | 1380 | 0.20 |
| 11 | 5.0/5.0 | 235/300 | 24/24/24/23 | 450/460 | 1000 | 775 | 0.40 |
| 12 | 2.5/2.5 | 185/190 | 104/76/30/23 | 460/425 | 1200 | 1860 | 0.20 |
| 13 | 2.5/2.5 | 65/115 | 86/69/28/23 | 460/360 | 1250 | 1940 | 0.20 |
| 14 | 3.6/1.6 | 155/140 | 69/60/27/24 | 400/360 | 950 | 1415 | 0.20 |
| 15 | 2.5/2.5 | 130/165 | 56/51/26/24 | 400/380 | 800 | 1240 | 0.20 |
| 16 | 1.6/3.6 | 120/175 | 76/51/26/23 | 400/380 | 1100 | 1640 | 0.20 |
| 17 | 2.5/2.5 | 75/70 | 26/25/25/25 | 0/0 | 1250 | 1940 | 0.20 |
| 18 | 2.5/2.5 | 150/110 | 29/27/26/24 | 0/0 | 1450 | 2250 | 0.20 |
| 19 | 2.5/2.5 | 195/180 | 26/24/24/23 | 0/0 | 1200 | 1860 | 0.20 |
| 20 | 2.5/2.5 | 140/385 | 74/61/24/23 | 400/400 | 300 | 465 | 0.20 |

TABLE 4-continued

| | | | Extrusion Conditions | | | | | |
|---|---|---|---|---|---|---|---|---|
| 21 | 5.0 | 235 | 89/74/70/36 | 372/371 | 2500 | 3900 | 0.20 |
| 22 | 5.0 | 655 | 23/21/20/21 | 0/0 | 600 | 930 | 0.20 |
| 23 | 5.0 | 185 | 23/21/20/21 | 390/390 | 1500 | 2300 | 0.20 |
| 24 | 5.0 | 120/170 | 22/22/22/21 | 400/400 | 1000 | 1550 | 0.20 |
| 25 | 5.0 | — | — | — | 1800 | 2800 | 0.15 |
| 26 | 5.0 | — | 30/63/70/79 | 227/224 | 1900 | — | 0.20 |
| 27 | 0.4/4.6 | — | 34/70/78/84 | 280/250 | 1700 | — | 0.20 |
| 28 | 0.9/4.1 | — | 34/71/80/80 | 272/248 | 1800 | — | 0.20 |
| 29 | 1.6/3.4 | — | 34/71/79/80 | 269/240 | 1800 | — | 0.20 |
| 30 | 0.4/4.6 | — | 31/70/79/79 | 287/281 | 2000 | — | 0.20 |
| 31 | 1.5/3.5 | — | 28/37/38/45 | 317/323 | 1200 | — | 0.20 |

TABLE 5

Fiber Properties

| Sample | Fiber Diameter (microns) | Peak Tensile Stress (MPa) N = 15 | Std Dev | Comments |
|---|---|---|---|---|
| 1 | 21.9 | 234.0 | 74 | Untacky Fiber tow collected |
| 2 | 16.3 | 292.0 | 159 | Untacky Fiber tow collected |
| 3 | 10.1 | 219.8 | 94 | Untacky fine fibers collected |
| 4 | 26.6 | 124.0 | 35 | Fibers broke >200 m/m |
| 7 | — | — | — | Non Tacky, Fibers broke >500 m/m |
| 8 | — | — | — | Heated Upper Air in column improved Spinning |
| 9 | — | — | — | Frequent Fiber breaks |
| 12 | 18.3 | 144.0 | 35 | — |
| 13 | 16.0 | 167.0 | 49 | — |
| 14 | 22.3 | 127.0 | 30 | — |
| 15 | 18.3 | 159.0 | 20 | 800 m/min most stable |
| 16 | 16.7 | 204.0 | 31 | — |
| 17 | 20.3 | 102.3 | 19 | Some crimp and bulk in fiber; Ran well with Air off |
| 18 | 15.3 | 157.0 | 46 | Lots of micro crimp and bulkiness; Ran well with Air off |
| 19 | 15.9 | 148.3 | 21 | Some crimp and bulk in fiber; Ran well with Air off |
| 20 | — | — | — | Corkscrewing on spin plate; inferior fiber formation |
| 21 | 11.0 | 283.8 | 38 | Stable spinning at 2000-2400 m/min |
| 22 | 28.1 | 257.0 | 89 | Very viscous, very slow fiber drop, pump kick out, non tacky fibers |
| 23 | 12.0 | 230.0 | 65 | Fibers little tacky even at high cold air flow |
| 24 | 16.9 | 176.0 | 75 | Fibers little tacky even at high cold air flow. |
| 25 | 11.7 | 133.0 | 15 | Control Run on Fiber Grade Polypropylene |
| 26 | 12.9 | 286.4 | 42 | Control Run on Fiber Grade PLA |
| 27 | 13.4 | 265.0 | 20 | — |
| 28 | 14.5 | 240.0 | 68 | — |
| 29 | 18.2 | — | — | — |
| 30 | 12.9 | 251.0 | 37 | — |
| 31 | 12.6 | 195.0 | 28 | — |

TABLE 6

Fiber Properties (cont.)

| | | | | DSC Evaluation at 10° C./min | | | |
|---|---|---|---|---|---|---|---|
| Sample | Tenacity (g/denier) | Peak Load ($g_f$) | % Elongation | $1^{st}$ Heat of Fusion (J/g) | Melt Temp 1 (° C.) | $2^{nd}$ Heat of Fusion (J/g) | Melt Temp 2 (° C.) |
| 1 | 2.12 | 9.30 | 64.5 | 35.54 | 112.10 | 21.88 | 162.8 |
| 2 | 2.64 | 6.47 | 56.0 | 37.16 | 112.30 | 23.30 | 162.4 |
| 3 | 1.99 | 1.86 | 68.0 | 74.50 | 113.20 | — | — |
| 4 | 1.12 | 7.12 | 107.0 | — | — | — | — |
| 5 | 1.51 | 3.70 | 38.7 | — | — | — | — |
| 6 | 1.53 | 3.70 | 43.0 | 19.48 | 113.00 | 21.07 | 159.5 |
| 12 | 1.30 | 3.94 | 54.7 | 27.25 | 113.20 | 27.40 | 163.3 |
| 13 | 1.51 | 3.52 | 36.4 | 33.36 | 112.82 | 28.19 | 163.3 |
| 14 | 1.15 | 5.26 | 69.5 | 44.16 | 113.45 | 17.42 | 163.1 |
| 15 | 1.44 | 4.30 | 48.9 | 26.39 | 113.40 | 24.70 | 163.8 |
| 16 | 1.85 | 4.65 | 50.5 | 11.36 | 113.10 | 35.07 | 164.7 |
| 17 | 0.93 | 3.30 | 289.0 | 65.80 | 114.60 | — | — |
| 18 | 1.42 | 3.17 | 163.0 | 67.90 | 114.30 | — | — |

TABLE 6-continued

Fiber Properties (cont.)

| | | | | DSC Evaluation at 10° C./min | | | |
|---|---|---|---|---|---|---|---|
| Sample | Tenacity (g/denier) | Peak Load (g_f) | % Elongation | 1st Heat of Fusion (J/g) | Melt Temp 1 (° C.) | 2nd Heat of Fusion (J/g) | Melt Temp 2 (° C.) |
| 19 | 1.34 | 2.99 | 246.0 | 63.50 | 114.30 | — | — |
| 21 | 2.57 | 2.77 | 34.7 | 51.02 | 167.40 | — | — |
| 22 | 2.33 | 15.8 | 282.0 | — | — | — | — |
| 23 | 2.09 | 2.70 | 157.0 | — | — | — | — |
| 24 | 1.60 | 3.99 | 57.1 | — | — | — | — |
| 25 | 2.19 | 1.45 | 205.0 | — | — | — | — |
| 26 | 2.60 | 4.05 | 43.3 | 52.40 | 164.60 | — | — |
| 27 | 2.40 | 3.85 | 50.5 | 7.05 | 112.00 | 44.60 | 164.2 |
| 28 | 2.17 | 3.96 | 64.7 | 11.41 | 112.20 | 44.27 | 164.1 |
| 29 | 1.57 | 4.56 | 40.3 | 31.60 | 112.80 | 31.36 | 163.8 |
| 30 | 2.27 | 3.45 | 45.5 | negligible | — | 50.02 | 165.2 |
| 31 | 1.77 | 2.51 | 14.9 | 34.35 | 113.30 | 30.00 | 164.3 |

TABLE 7

Commercial Fiber Properties

| Name | Mfg. | Type | Polymers | Fiber Size (microns) | Tenacity (g/denier) | Peak Load (g_f) | % Elongation | 1st Heat of Fusion (J/g) | Melt Temp 1 (° C.) | 2nd Heat of Fusion (J/g) | Melt Temp 2 (° C.) |
|---|---|---|---|---|---|---|---|---|---|---|---|
| ESC-215A | ES Fibervisions | Bi-comp. | PE/PP | 16.6 | 3.8 | 7.3 | 70.9 | 69.00 | 128.0 | 47.60 | 169.0 |
| PL80 | Unitika Ltd. | Bi-comp. | PLA1/PLA2 | 17.5 | 1.7 | 4.6 | 26.9 | 10.64 | 132.0 | 25.86 | 160.0 |
| ESC-806 ALAD | ES Fibervisions | Bi-comp. | PE/PP (65/35) | 15.7 | — | — | — | 111.20 | 130.5 | 34.44 | 158.5 |
| T-255 | Kosa Inc. | Bi-comp. | PE/PET | 18.4 | — | — | — | 72.60 | 128.5 | 24.40 | 240.4 |

As indicated above, the bicomponent fibers produced according to the present invention had a size, tenacity and % elongation similar to commercially available fibers. Further, the melt peak difference of bicomponent fibers produced herein was in the range of approximately 50° C., while most commercial bicomponent fibers had a melt peak difference in the range of about 30-40° C.

Example 3

Several of the bicomponent fibers of Example 2 were cut into 6-mm staple fibers and airlaid in the form of unbonded nonwoven webs. Further, the following commercially available fibers were also formed into airlaid webs for comparative purposes: (1) Celbond® T-255—bicomponent fibers having a polyethylene sheath and a polyester core, which are available from KoSa, Inc. of Charlotte, N.C.; (2) ESC-806 ALAD—bicomponent fibers having a polyethylene sheath and polypropylene core available from ES Fibervision, Inc. of Athens, Ga.; and (3) Terramac™ PL80-polylactic acid bicomponent fibers available from Unitika Ltd. of Osaka, Japan. Some of the samples employed a 50%/50% blend of the bicomponent fibers with 1.5 denier per filament (dpf) Tencel® H215 963 type fibers having a 6-mm staple length (Tencel® fibers available from Lenzing Fibers Inc. of Axis, Ala.), while other samples utilized 100% bicomponent fibers. The airlaid webs were then through air bonded (TAB) at a time and temperature combination to facilitate bonding. The bonded webs were cut into 1"×5" strips to perform tensile testing to evaluate the bonding efficacy. The results are set forth below in Tables 8-9.

TABLE 8

Tensile Properties of 50% Multicomponent Fiber and 50% TENCEL Fiber Web

| | Fiber Description | | | | | | Bonding | | Web Tensile Properties | | | | |
|---|---|---|---|---|---|---|---|---|---|---|---|---|---|
| Sample | Sheath Polymer | Core Polymer | Configuration | Fiber % | Other constituent Fiber | Total Basis Weight (g/m²) | TAB Time (sec) | TAB temperature (° C.) | Peak Load (g_f/inch) | % Elongation | Energy To Peak load | Elongation at Break | % Area Shrinkage |
| 13 | P2 | P10 | Sheath/Core | 50 | TENCEL (H215 963) 1.5 dpf, 6 mm | 24.86 | 120 | 115 | 64.8 | 10.65 | 0.0320 | 0.320 | — |
| | | | | | | 25.36 | 120 | 125 | 88.6 | 7.93 | 0.0360 | 0.240 | — |
| | | | | | | 24.54 | 120 | 140 | 85.2 | 11.86 | 0.0460 | 0.360 | — |
| | | | | | | 25.51 | 120 | 160 | 144.3 | 3.92 | 0.0290 | 0.120 | — |

TABLE 8-continued

Tensile Properties of 50% Multicomponent Fiber and 50% TENCEL Fiber Web

| | Fiber Description | | | | | Bonding | | | Web Tensile Properties | | | | |
|---|---|---|---|---|---|---|---|---|---|---|---|---|---|
| Sample | Sheath Polymer | Core Polymer | Configuration | Fiber % | Other constituent Fiber | Total Basis Weight (g/m²) | TAB Time (sec) | TAB temperature (° C.) | Peak Load (g/inch) | % Elongation | Energy To Peak load | Elongation at Break | % Area Shrinkage |
| 12 | P3 | P10 | Sheath/Core | 50 | TENCEL (H215 963) 1.5 dpf, 6 mm | 25.30 | 120 | 115 | 222.7 | 10.63 | 0.1080 | 0.320 | — |
| | | | | | | 24.50 | 120 | 125 | 328.4 | 12.90 | 0.1940 | 0.400 | — |
| | | | | | | 24.50 | 120 | 140 | 385.2 | 14.20 | 0.2770 | 0.430 | — |
| | | | | | | 26.10 | 120 | 160 | 425.0 | 10.30 | 0.2370 | 0.310 | — |
| | T-255 | | | 50 | TENCEL (H215 963) 1.5 dpf, 6 mm | 24.70 | 120 | 115 | | No Bonding observed | | | |
| | | | | | | 24.20 | 120 | 125 | | No Bonding observed | | | |
| | | | | | | 27.00 | 120 | 140 | 276.1 | 7.96 | 0.1090 | 0.240 | — |
| | | | | | | 26.80 | 120 | 160 | 561.3 | 9.68 | 0.2570 | 0.250 | — |
| | PL80 | | | 50 | TENCEL (H215 963) 1.5 dpf, 6 mm | 25.10 | 120 | 115 | | No Bonding observed | | | |
| | | | | | | 25.90 | 120 | 130 | 1.44 | 0.0030 | 0.043 | 3.33 | |
| | | | | | | 25.00 | 120 | 140 | 51.5 | 2.23 | 0.0053 | 0.067 | 4.17 |
| | | | | | | 23.40 | 120 | 160 | 80.4 | 2.18 | 0.0070 | 0.065 | 4.17 |
| | | | | | | 24.40 | 120 | 170 | 132.2 | 4.57 | 0.0280 | 0.140 | 4.17 |

TABLE 9

Tensile Properties of 100% Multicomponent Fiber Web

| Sample | Sheath Polymer | Core Polymer | Configuration | Fiber % | Total Basis Weight (g/m²) | TAB Time (sec) | TAB Temperature (° C.) | Peak Load (g/inch) | % Elongation | Energy to Peak load (lb_f * inch) | Elongation at Break (inches) | % Area Shrinkage |
|---|---|---|---|---|---|---|---|---|---|---|---|---|
| 12 | P3 | P10 | Sheath/Core | 100 | 26.00 | 30 | 115 | 1472 | 16.54 | — | — | 3.33 |
| | | | | | 71.60 | 30 | 115 | 4640 | 19.9 | — | — | 5.75 |
| | | | | | 70.50 | 30 | 125 | 5568 | 26.7 | 6.50 | 0.800 | 4.17 |
| | | | | | 26.90 | 30 | 125 | 1614 | 25.2 | 1.72 | 0.760 | 4.17 |
| | | | | | 23.20 | 30 | 140 | 1491 | 26.9 | 1.75 | 0.810 | 8.90 |
| | | | | | 23.20 | 30 | 160 | 1418 | 27.2 | 1.75 | 0.820 | 10.16 |
| | | | | | 24.10 | 30 | 180 | | Web Melted >95% shrinkage | | | |
| 15 | P3 | P10 | Side-by-Side 50-50 | 100 | 72.10 | 30 | 125 | 4682 | 28.01 | 5.64 | 0.840 | 4.17 |
| | | | | | 28.06 | 30 | 125 | 1468 | 29.04 | 1.81 | 0.870 | 4.17 |
| 16 | P3 | P10 | Side-by-Side 30-70 | 100 | 73.60 | 30 | 125 | 4650 | 23.5 | 4.90 | 0.710 | 6.65 |
| | | | | | 57.50 | 30 | 125 | 3377 | 28.7 | 4.44 | 0.860 | — |
| | | | | | 28.30 | 30 | 125 | 1264 | 22.6 | 1.24 | 0.680 | 6.65 |
| 14 | P3 | P10 | Side by Side 70-30 | 100 | 71.30 | 60 | 125 | 3414 | 22.85 | 3.27 | 0.670 | 10.16 |
| | | | | | 26.70 | 30 | 125 | 1441 | 32.4 | 1.90 | 0.970 | 12.10 |
| PL-80 | | PLA1 sheath/PLA2 core | | 100 | 24.20 | 30 | 95 | | Web shrunk drastically | | | 79.60 |
| | | | | | 25.00 | 30 | 115, 125 | | Web shrunk and melted | | | >80% |
| ESC806 ALAD | | PE/PP | 65% sheath/ 35% core | 100 | 25.25 | 30 | 115, 125 | | No bonding observed | | | |
| | | | | | 30.10* | 30 | 140 | 3141 | 17.1 | 2.27 | 0.514 | 19.70 |
| | | | | | 33.90* | 30 | 160 | 3264 | 21.9 | 3.12 | 0.658 | 58.00 |
| | | | | | 25.00 | 30 | 180 | | Web Melted | | | >80% |
| T-255 | | PE/PET | | 100 | 24.40 | 30 | 115, 125 | | No bonding observed | | | |
| | | | | | 25.10 | | | | | | | |
| | | | | | 71.00 | | | | | | | |
| | | | | | 70.30 | 30 | 140 | 2559 | 36.2 | 3.99 | 1.090 | 3.33 |
| | | | | | 27.80 | 30 | 140 | 1145 | 48.3 | 2.03 | 1.450 | 4.17 |
| | | | | | 28.70 | 30 | 160 | 1213 | 52.3 | 2.05 | 1.590 | 6.60 |
| | | | | | 29.20 | 30 | 180 | 1309 | 46.0 | 2.38 | 1.390 | 6.60 |

*Basis weight increased from target 25 g/m² due to shrinkage

Figure 2A:
FIG. 2a shows Sample No. 13
Figure 2B:
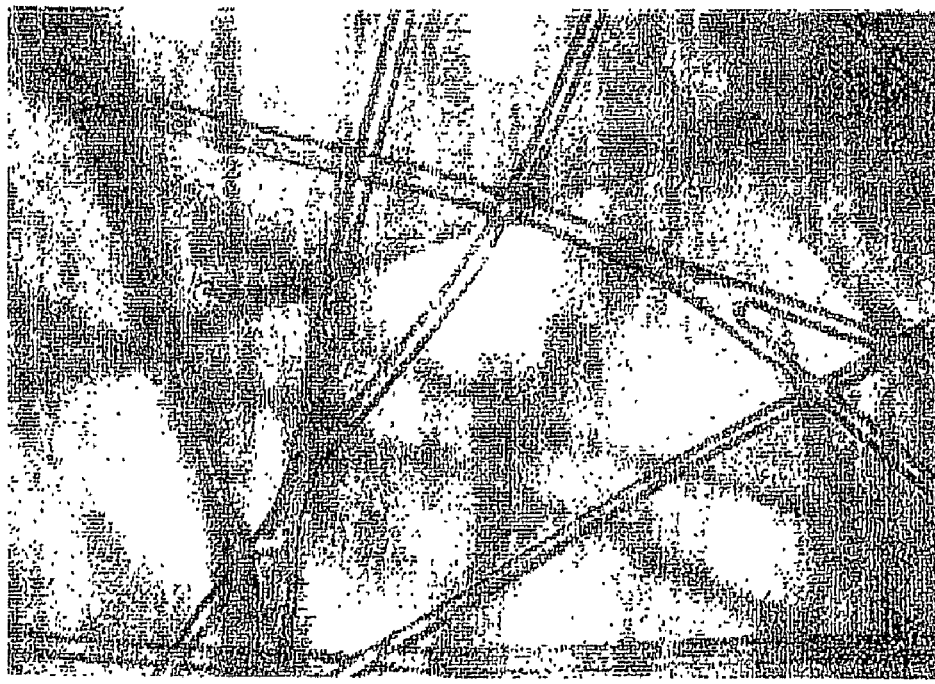
FIG. 2b shows Sample No. 12.

As indicated, the bicomponent fibers of the present invention exhibited a good balance of web tensile strength, bonding window, and low bonding temperature. For example, the fibers exhibited better binding properties at lower temperatures than the commercial airlaid grade binders, such as the T-255 and PLA fibers. Lower binding temperatures may result in lower heating costs, higher speeds of bonding (converting), and softer webs. Even at relatively low temperatures of 95° C. and 115° C., the PL80 fibers resulted in an undesirable nonwoven area shrinkage of 80% or more. In contrast, the fibers of the present invention shrunk to a much lesser extent. It is worth mentioning that some fibers formed according to the present invention had a relatively low tensile strength. For example, an SEM microphotograph (40×) of the web formed using the fibers of Sample No. 13 (Table 8) is shown in FIG. 2a. Beading of the sheath polymer was found upon analysis of the microphotograph, which is believed to be a result of the high surface tension and low viscosity of the sheath polymer melt. For enhanced bonding, the melted sheath polymer optimally flows to the fiber junction points and form welds as shown in FIG. 2b (Sample No. 12 (Table 8)). Furthermore, the sheath polymer used in of Sample No.

13 (Table 8) showed a slight tendency to form tacky fibers due to its low molecular weight.

Example 4

The ability to form bicomponent fiber webs in accordance with the present invention was demonstrated. Specifically, several of the fibers of Example 2 were cut into 6-millimeter staple fibers and airlaid in the form of unbonded nonwoven webs having the size of 12"×4". Commercial bicomponent fibers (i.e., T-255 from Invista) were also tested as a control. The airlaid webs were then subjected to through air bonding (TAB) at 125° C. for 30 seconds. Various properties were then measured, including the pre- and post-stabilization density, i.e., the density before and after through-air bonding. The densities were measured by averaging the thickness along four (4) locations throughout the length of the web. The pre-stabilization of the webs (at a pressure of about 0.05 pounds per square inch) was between web densities of 0.07 and 0.08 grams per cubic centimeter. The remaining results are set forth below in Table 10.

TABLE 10

Side-By-Side Biodegradable Bicomponent Fiber Web Properties

| Sample | Bicomponent Fiber Polymer A | Bicomponent Fiber Polymer B | Configuration | Basis Weight (g/m$^2$) | Post Stabilization Density at 0.05 psi (g/cm$^3$) | Average Bulk (mm) |
|---|---|---|---|---|---|---|
| 12 | P3 | P10 | 50% Core B | 71.6 | 0.0394 | 1.82 |
|    |    |     | 50% Sheath A | 69.8 | 0.0375 | 1.86 |
|    |    |     |              | 73.0 | 0.0412 | 1.77 |
|    |    |     |              | 26.8 | 0.0297 | 0.90 |
| 15 | P3 | P10 | 50% Side A | 75.8 | 0.0249 | 3.04 |
|    |    |     | 50% Side B | 25.8 | 0.0176 | 1.46 |
| 16 | P3 | P10 | 30% Side A | 75.2 | 0.0228 | 3.29 |
|    |    |     | 70% Side B | 26.5 | 0.0204 | 1.30 |
| 14 | P3 | P10 | 70% Side A | 76.8 | 0.0270 | 2.77 |
|    |    |     | 30% Side B | 74.9 | 0.0273 | 2.72 |
|    |    | T-255 |            | 70.3 | 0.0312 | 2.25 |
|    |    |     |              | 78.5 | 0.0301 | 2.60 |
|    |    |     |              | 28.1 | 0.0178 | 1.58 |

As indicated, side-by-side fibers formed according to the present invention formed a relatively bulky web. For example, the sheath/core fiber of Example No. 12 (~70 gsm) had a bulk of 1.8 millimeter, while the side-by-side fibers had a bulk ranging from 2.7 to 3.3 millimeters, thus providing more void volume. It is worth noting that the T-255 fibers possessed some crimps that gave it an enhanced pre-bonding bulk.

Example 5

Figure 3:
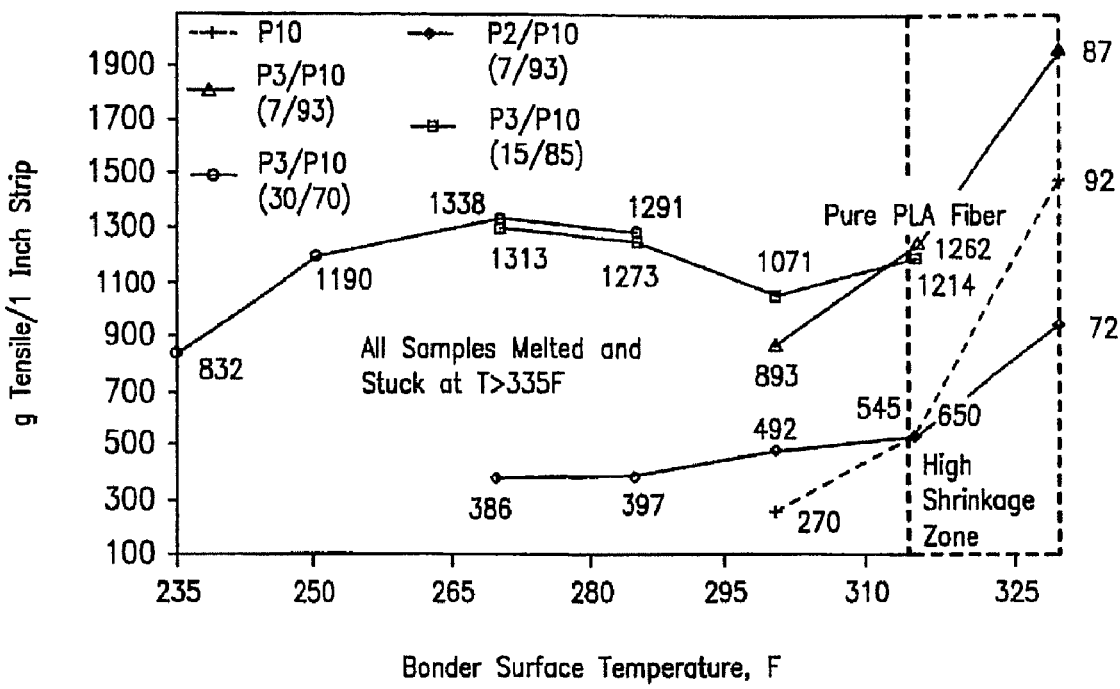
FIG. 3 is a graph depicting strip tensile strength versus bonding temperature for the point-bonded webs of Example 5 having a basis weight of 25 $g/m^2$.
Figure 4:
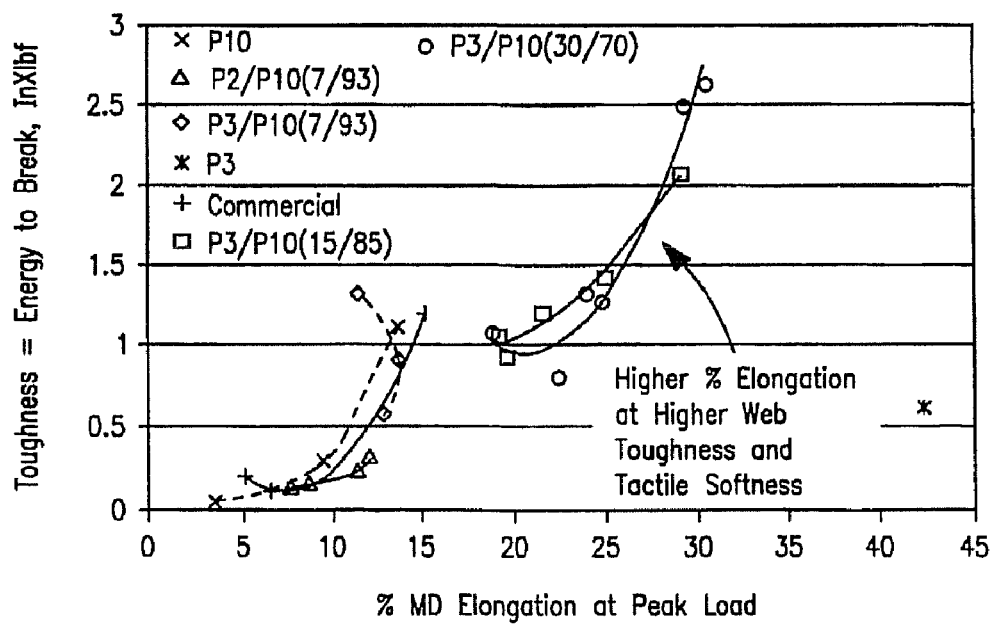
FIG. 4 is a graph depicting toughness versus % elongation for the point-bonded webs of Example 5 having a basis weight of 25 $g/m^2$.

Several of the fibers of Example 2 were airlaid as described in Example 2, but bonded over "wire weave" point bond patterns in a carver press at a fixed pressure, temperature and time interval. The fibers were initially cut to a length of 6 mm using a die and opened in a web former. 0.85 grams of the opened fibers were collected in a 4"×12" strip from the former that was placed on a wire weave bond patterned surface. A press was set up at a certain temperature (112° C. to 158° C.), with the upper plate being set to a temperature of 35° C. lower than the press to minimize web sticking. The strip was placed on the press and then compressed at 14,000 pounds per square inch for 5 seconds. The bonded strip was gently removed from the bond pattern surface and cut into six different 1"×5" strips for strip tensile testing. The results are shown in Tables 11-13 and FIGS. 3-4.

TABLE 11

Fiber Properties (Pump rpm = 5)

| Exp # | Polymer A | Polymer B | Mix | A/B | Melt Flow Index | Uptake Speed (m/min) | Diameter (microns) | Tenacity (g/denier) | Elongation |
|---|---|---|---|---|---|---|---|---|---|
| 17 | P2 |  | Mono | — | 150.0 | 1250 | 20.30 | 0.93 | 289.00 |
| 19 | P3 |  | Mono | — | 48.3 | 1200 | 15.70 | 1.34 | 246.00 |
| 26 |    | P10 | Mono | — | 10.8 | 1900 | 13.20 | 2.60 | 43.30 |
| —  | —  | P10 | Mono | — |       | 2500 | 11.02 | 2.60 | 34.70 |
| 30 | P2 | P10 | Blend | 7/93 | 12.7 | 750 | 17.70 | 2.41 | 49.70 |
| 31 | P2 | P10 | Blend | 30/70 | 23.7 | — | — | — | — |
| 27 | P3 | P10 | Blend | 7/93 | 12.1 | 1350 | 15.20 | 2.18 | 56.50 |
| 28 | P3 | P10 | Blend | 15/85 | 13.6 | 850 | 16.30 | 1.95 | 67.70 |

TABLE 11-continued

| | | | Fiber Properties (Pump rpm = 5) | | | | | |
|---|---|---|---|---|---|---|---|---|
| 29 | P3 | P10 | Blend 30/70 | 20.5 | 600 | 22.70 | 1.78 | 81.80 |
| | | | | | 2400 | 11.60 | 2.40 | 33.29 |
| | | | | | 2800 | 10.20 | 2.40 | 27.10 |

| Exp # | Peak Load (g$_f$/inch) | Low melt Peak (° C.) | Low Melt Peak area (J/g) | High melt Peak (° C.) | High Melt Peak area (J/g) | High Melt Half Peak width (° C.) | Comment |
|---|---|---|---|---|---|---|---|
| 17 | 3.32 | 114.50 | 73.60 | — | — | — | — |
| 19 | 2.99 | 114.30 | 71.80 | — | — | — | — |
| 26 | 4.05 | — | — | 164.60 | 52.44 | 6.4 | — |
| — | 2.77 | — | — | 166.80 | 51.02 | — | Unstable run |
| 30 | 6.69 | 112.00 | neg | 168.14 | 45.05 | 9.1 | Shoulder formed |
| 31 | — | — | — | — | — | — | — |
| 27 | 4.51 | neg | neg | 168.37 | 48.70 | 9.2 | Double Peak Formed |
| 28 | 4.57 | 110.80 | 4.04 | 167.20 | 43.76 | — | — |
| 29 | 8.67 | 110.43 | 20.95 | 167.60 | 37.07 | — | — |
| | 2.90 | 112.30 | 15.82 | 164.70 | 38.80 | — | short test run |
| | 2.14 | — | — | — | — | — | short test run |

TABLE 12

Strip Tensile Properties

| Press, 14000 psi, 5 sec | | P10 | | | | P2/P10 Sheath/core (7%/93%) | | | | P3/P10 Sheath/core (7%/93%) | | | |
|---|---|---|---|---|---|---|---|---|---|---|---|---|---|
| Lower Platten Temp (° F.) | Upper Platten Temp (° F.) | Tensile (g$_f$) | Std. dev. | % Elongation | Energy to Break (in * lb$_f$) | Tensile (g$_f$) | Std. dev. | % Elongation | Energy to Break (in * lb$_f$) | Tensile (g$_f$) | Std. dev. | % Elongation | Energy to Break (in * lb$_f$) |
| 235 | 200 | — | — | — | — | — | — | — | — | — | — | — | — |
| 250 | 215 | — | — | — | — | — | — | — | — | — | — | — | — |
| 270 | 235 | — | — | — | — | 386 | 45.8 | 7.7 | 0.1160 | — | — | — | — |
| 285 | 250 | — | — | — | — | 397 | 51.0 | 8.7 | 0.1480 | — | — | — | — |
| 300 | 265 | 270 | 75 | 3.3 | 0.0386 | 492 | 92.0 | 11.4 | 0.2199 | 893 | 223 | 12.9 | 0.571 |
| 315 | 280 | 550 | 120 | 9.6 | 0.2793 | 546 | 172.0 | 12.0 | 0.3060 | 1262 | 257 | 13.7 | 0.904 |
| 330 | 295 | 1492 | 187.3 | 13.6 | 1.113 | — | — | — | — | 1987 | 501 | 11.5 | 1.322 |

| Press, 14000 psi, 5 sec | | P3/P10 Sheath/core (15%/85%) | | | | P3/P10 Sheath/core (30%/70%) | | | |
|---|---|---|---|---|---|---|---|---|---|
| Lower Platten Temp (° F.) | Upper Platten Temp (° F.) | Tensile (g$_f$) | Std. dev. | % Elongation | Energy to Break, in * lbf | Tensile (g$_f$) | Std. dev. | % Elongation | Energy to Break (in * lb$_f$) |
| | 235 | 200 | — | — | — | — | 832 | 133.0 | 22.4 | 0.7780 |
| | 250 | 215 | — | — | — | — | 1190 | 206.0 | 24.8 | 1.2435 |
| | 270 | 235 | 1313 | 136.0 | 25.2 | 1.397 | 1338 | 299.0 | 18.9 | 1.0610 |
| | 285 | 250 | 1273 | 286.2 | 21.6 | 1.190 | 1291 | 236.5 | 24.0 | 1.3030 |
| | 300 | 265 | 1071 | 108.2 | 19.7 | 0.918 | stuck on platten | — | — | — |
| | 315 | 280 | 1214 | 107.1 | 19.3 | 1.050 | — | — | — | — |
| | 330 | 295 | stuck on platten | — | — | — | — | — | — | — |

TABLE 13

Strip Tensile Properties (cont.)

| Press, 18000 psi, 5 sec | | P3 | | | | Commercial Bicomponent Fibers* | | | |
|---|---|---|---|---|---|---|---|---|---|
| Lower Platten Temp (° F.) | Upper Platten Temp (° F.) | Tensile (g$_f$) | Std. dev. | % Elongation | Energy to Break (in * lb$_f$) | Tensile (g$_f$) | Std. dev. | % Elongation | Energy to Break (in * lb$_f$) |
| 210 | 210 | 371.9 | 75.5 | 42.4 | 0.603 | — | — | — | — |
| 230 | 230 | — | — | — | — | 388 | 62.6 | 6.5 | 0.107 |
| 240 | 240 | — | — | — | — | 867 | 136.0 | 5.2 | 0.176 |
| 255 | 255 | — | — | — | — | 1882 | 139.0 | 15.2 | 1.210 |

TABLE 13-continued

Strip Tensile Properties (cont.)

| Press, 18000 psi, 5 sec | | P3/P10 Sheath/core (15%/85%) | | | | P3/P10 Sheath/core (30%/70%) | | |
|---|---|---|---|---|---|---|---|---|
| Lower Platten Temp (° F.) | Upper Platten Temp (° F.) | Tensile (g$_f$) | Std. dev. | % Elongation | Energy to Break (in * lb$_f$) | Tensile (g$_f$) | Std. dev. | % Elongation |
| 210 | 210 | — | — | — | — | — | — | — |
| 230 | 230 | — | — | — | — | — | — | — |
| 240 | 240 | 1302.0 | 117.0 | 21.7 | 1.199 | 2199.0 | 134 | 30.6 |
| 255 | 255 | 1724.3 | 176.3 | 29.2 | 2.040 | 2130.3 | 297 | 29.4 |

*Bicomponent fibers available from Far Eastern Textiles Ltd. of Taipei, Taiwan.

As indicated, fibers containing 100% polylactic acid resulted in webs that a relatively low strength and % elongation. At higher bonding temperatures the web tensile increased, but the web became stiff. In contrast, webs formed with the fibers of the present invention were relatively strong, had a high % elongation, and were soft.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A biodegradable multicomponent fiber comprising:
   a first component that contains at least one high-melting point aliphatic polyester having a melting point of from about 160° C. to about 250° C.;
   a second component that contains at least one low-melting point aliphatic polyester, the melting point of the low-melting point aliphatic polyester being at least about 30° C. less than the melting point of the high-melting point aliphatic polyester, wherein the low-melting point aliphatic polyester has a number average molecular weight of from about 30,000 to about 120,000 Daltons and an apparent viscosity of from about 50 to about 215 Pascal-seconds, as determined at a temperature of 160° C. and a shear rate of 1000 sec$^{-1}$, wherein the second component is free of a multicarboxylic acid nucleating agent.

2. The biodegradable multicomponent fiber of claim 1, wherein the high-melting point aliphatic polyester has a melting point of from about 180° C. to about 220° C.

3. The biodegradable multicomponent fiber of claim 1, wherein the high-melting point aliphatic polyester is polylactic acid.

4. The biodegradable multicomponent fiber of claim 1, wherein the low-melting point aliphatic polyester has an apparent viscosity of from about 75 to about 200 Pascal-seconds, as determined at a temperature of 160° C. and a shear rate of 1000 sec$^{-1}$.

5. The biodegradable multicomponent fiber of claim 1, wherein the low-melting point aliphatic polyester has an apparent viscosity of from about 80 to about 150 Pascal-seconds, as determined at a temperature of 160° C. and a shear rate of 1000 sec$^{-1}$.

6. The biodegradable multicomponent fiber of claim 1, wherein the low-melting point aliphatic polyester has a melting point at least about 40° C. less than the melting point of the high-melting point aliphatic polyester.

7. The biodegradable multicomponent fiber of claim 1, wherein the low-melting point aliphatic polyester has a melting point of from about 120° C. to about 160° C.

8. The biodegradable multicomponent fiber of claim 1, wherein the low-melting point aliphatic polyester has a number average molecular weight of from about 40,000 to about 100,000 Daltons.

9. The biodegradable multicomponent fiber of claim 1, wherein the low-melting point aliphatic polyester has a polydispersity index of from about 1.0 to about 3.0.

10. The biodegradable multicomponent fiber of claim 1, wherein the low-melt point aliphatic polyester has a melt flow index of from about 20 to about 120 grams per 10 minutes, measured at a force of 2160 grams and temperature of 190° C. in accordance with ASTM Test Method D1238-E.

11. The biodegradable multicomponent fiber of claim 1, wherein the fiber has a tenacity of from about 0.75 to about 7.0 grams-force per denier.

12. The biodegradable multicomponent fiber of claim 1, wherein the fiber has a peak tensile stress of from about 150 to about 500 Megapascals.

13. The biodegradable multicomponent fiber of claim 1, wherein the fiber has a peak tensile stress of from about 200 to about 400 Megapascals.

14. The biodegradable multicomponent fiber of claim 1, wherein the low-melting point aliphatic polyester has a glass transition temperature of less than about 50° C.

15. The biodegradable multicomponent fiber of claim 1, wherein the low-melting point aliphatic polyester has a glass transition temperature of less than about 0° C.

16. The biodegradable multicomponent fiber of claim 1, wherein the low-melting point aliphatic polyester has a glass transition temperature of less than about −10° C.

17. The biodegradable multicomponent fiber of claim 1, wherein the low-melting point aliphatic polyester contains from about 10 mol. % to about 40 mol. % of an aromatic monomer constituent.

18. The biodegradable multicomponent fiber of claim 1, wherein the aliphatic polyester constitutes at least about 95 wt. % of the second component.

19. The biodegradable multicomponent fiber of claim 1, wherein the low-melting point aliphatic polyester is polybutylene succinate.

20. The biodegradable multicomponent fiber of claim 1, wherein the fiber has a sheath/core or side-by-side configuration.

21. A method for forming the multicomponent fiber of claim 1, the method comprising:
   extruding a first thermoplastic composition, the first thermoplastic composition comprising the high-melting point aliphatic polyester; and extruding a second thermoplastic composition, the second thermoplastic composition comprising the low-melting point aliphatic polyester, wherein the second thermoplastic composition is extruded at a temperature ranging from about 120° C. to about 200° C.; and quenching the extruded thermoplastic compositions; and drawing the extruded and quenched thermoplastic compositions.

22. The method of claim 21, wherein the second thermoplastic composition is extruded at a temperature ranging from about 145° C. to about 195° C.

23. The method of claim 21, wherein the fiber is drawn at a ratio of from about 200:1 to about 6000:1.

24. A nonwoven web comprising biodegradable multicomponent fibers, wherein the multicomponent fibers comprise:
 a first component that contains at least one high-melting point aliphatic polyester having a melting point of from about 160° C. to about 250° C.;
 a second component that contains at least one low-melting point aliphatic polyester, the melting point of the low-melting point aliphatic polyester being at least about 40° C. less than the melting point of the high-melting point aliphatic polyester, wherein the low-melting point aliphatic polyester has a number average molecular weight of from about 30,000 to about 120,000 Daltons and an apparent viscosity of from about 50 to about 215 Pascal-seconds, as determined at a temperature of 160° C. and a shear rate of 1000 sec$^{-1}$, wherein the second component is free of a multicarboxylic acid nucleating agent.

25. The nonwoven web of claim 24, wherein the high-melting point aliphatic polyester has a melting point of from about 180° C. to about 220° C.

26. The nonwoven web of claim 24, wherein the high-melting point aliphatic polyester is polylactic acid.

27. The nonwoven web of claim 24, wherein the low-melting point aliphatic polyester has an apparent viscosity of from about 75 to about 200 Pascal-seconds, as determined at a temperature of 160° C. and a shear rate of 1000 sec$^{-1}$.

28. The nonwoven web of claim 24, wherein the low-melting point aliphatic polyester has an apparent viscosity of from about 80 to about 150 Pascal-seconds, as determined at a temperature of 160° C. and a shear rate of 1000 sec$^{-1}$.

29. The nonwoven web of claim 24, wherein the low-melting point aliphatic polyester has a melting point of from about 120° C. to about 160° C.

30. The nonwoven web of claim 24, wherein the low-melting point aliphatic polyester has a number average molecular weight of from about 45,000 to about 85,000 Daltons.

31. The nonwoven web of claim 24, wherein the low-melting point aliphatic polyester is polybutylene succinate.

32. The nonwoven web of claim 24, wherein the fibers have a peak tensile stress of from about 150 to about 500 Megapascals.

33. The nonwoven web of claim 24, wherein the fibers have a peak tensile stress of from about 200 to about 400 Megapascals.

34. An absorbent article comprising a substantially liquid-impermeable layer, a liquid-permeable layer, and an absorbent core, wherein the absorbent core, the liquid-permeable layer, or both comprise the nonwoven web of claim 24.

35. The biodegradable multicomponent fiber of claim 1, wherein the low-melting point aliphatic polyester has a number average molecular weight of from about 45,000 to about 85,000 Daltons.

36. The nonwoven web of claim 24, wherein the low-melting point aliphatic polyester has a number average molecular weight of from about 45,000 to about 85,000 Daltons.

* * * * *